United States Patent
Maguire et al.

(10) Patent No.: US 10,519,445 B2
(45) Date of Patent: Dec. 31, 2019

(54) INTRATHECAL DELIVERY OF NUCLEIC ACID SEQUENCES ENCODING ABCD1 FOR TREATMENT OF ADRENOMYELONEUROPATHY

(71) Applicant: The General Hospital Corporation, Boston, MA (US)

(72) Inventors: Casey A. Maguire, Arlington, MA (US); Florian Eichler, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 16/373,081

(22) Filed: Apr. 2, 2019

(65) Prior Publication Data
US 2019/0225967 A1    Jul. 25, 2019

Related U.S. Application Data

(63) Continuation of application No. 15/773,337, filed as application No. PCT/US2016/060375 on Nov. 3, 2016.

(60) Provisional application No. 62/300,691, filed on Feb. 26, 2016, provisional application No. 62/251,208, filed on Nov. 5, 2015.

(51) Int. Cl.
| | | |
|---|---|---|
| A61K 48/00 | (2006.01) | |
| A61P 25/28 | (2006.01) | |
| C12N 15/00 | (2006.01) | |
| C12N 15/86 | (2006.01) | |
| C12N 15/113 | (2010.01) | |
| A61K 9/00 | (2006.01) | |

(52) U.S. Cl.
CPC .......... *C12N 15/113* (2013.01); *A61K 9/0004* (2013.01); *A61K 9/0085* (2013.01); *A61K 48/005* (2013.01); *A61K 48/0075* (2013.01); *A61P 25/28* (2018.01); *C12N 15/86* (2013.01); *A61K 48/00* (2013.01); *C12N 2310/14* (2013.01); *C12N 2750/14141* (2013.01); *C12N 2750/14143* (2013.01); *C12N 2750/14152* (2013.01)

(58) Field of Classification Search
CPC ....... A61K 48/00; A61K 48/005; A61P 25/28; C12N 15/00; C12N 15/86; C12N 15/8645; C12N 2750/14111; C12N 2750/14141; C12N 2750/14143
See application file for complete search history.

(56) References Cited

U.S. PATENT DOCUMENTS

| | | | |
|---|---|---|---|
| 6,013,769 A * | 1/2000 | Mandel | C07K 14/47 530/300 |
| 6,225,525 B1 | 5/2001 | Leung et al. | |
| 7,192,579 B2 | 3/2007 | Allikmets et al. | |
| 2005/0032219 A1* | 2/2005 | Aubourg | A61K 38/1709 435/456 |
| 2013/0004471 A1 | 1/2013 | Denaro et al. | |
| 2013/0202559 A1 | 8/2013 | Skog et al. | |
| 2014/0010861 A1* | 1/2014 | Bancel | A61K 48/005 424/450 |

FOREIGN PATENT DOCUMENTS

| | | |
|---|---|---|
| WO | WO 2014/186579 | 11/2014 |
| WO | WO 2015/114365 | 8/2015 |

OTHER PUBLICATIONS

Gong et al, Mol. Ther. 23(5): 824-834, May 2015.*
Maguire et al, Mol. Therapy 16(10): 1695-1702, 2008.*
Ruzo et al, Human Gene Therapy 23: 1237-1246, 2012.*
Broekman et al, Neurosci. 138: 501-510, 2006.*
'www.ncbi.nlm.nih.gov' [online]. "X-Linked Adrenoleukodystrophy," dated Mar. 26, 1999, last updated on Feb. 15, 2018 [retrieved on Oct. 3, 2018]. Retrieved from the Internet: URL <https://www.ncbi.nlm.nih.gov/books/NBK1315/>. 19 pages.
Aubourg and Chaussain, "Adrenoleukodystrophy: The Most Frequent Genetic Cause of Addison's Disease," Horm Res, 2003, 59 Suppl 1:104-5.
Engelen et al., "X-linked adrenoleukodystrophy (X-ALD): clinical presentation and guidelines for diagnosis, follow-up and management," Orphanet J Rare Dis, 2012, 7: 51.
Gong et al., "Adenoassociated Vims Serotype 9-medialed Gene Therapy for X-Linked Adrenoleukodystrophy," Molecular Therapy, May 2015, 23: 824-834.
Gray et al., "Viral vectors and delivery strategies for CNS gene therapy," Ther Deliv, Oct. 2010, 1: 517-534.
International Preliminary Report on Patentability in International Application No. PCT/US2016/060375, dated May 8, 2018, 7 pages.
International Search report and Written Opinion in International Application No. PCT/US2016/060375, dated Feb. 27, 2017, 12 pages.
Katz et al., "Gene Therapy in Cardiac Surgery: Clinical Trials, Challenges, and Perspectives," Ann Thorac Surg, Jun. 2016, 101: 2407-2416.
Pujol et al., "Late onset neurological phenotype of the X-ALD gene inactivation in mice: a mouse model for adrenomyeloneuropathy," Hum Mol Genet, 2002, 11:499-505.

(Continued)

*Primary Examiner* — Kevin K Hill
(74) *Attorney, Agent, or Firm* — Fish & Richardson P.C.

(57) ABSTRACT

Methods of the invention encompass delivery of nucleic acid sequences encoding ABCD1 for the treatment of X-linked Adrenoleukodystrophy (X-ALD), e.g., for Adrenomyeloneuropathy (AMN).

10 Claims, 8 Drawing Sheets
Specification includes a Sequence Listing.

(56) References Cited

OTHER PUBLICATIONS

Simonato et al., "Progress in gene therapy for neurological disorders," Nature Reviews Neurology, 2013, 9: 277-291.
Steinberg et al., "Investigational Methods for Peroxisomal Disorders," Curr Protoc Hum Genet, Chapter 17:Unit 17.6, 2008, 23 pages.
Extended European Search Report in Application No. 16892990.5, dated Apr. 16, 2019, 10 pages.
Kohlschutter et al., "Novel Cytotoxic Vectors Based on Adeno-Associated Virus," Toxins, Dec. 2010, 2: 2754-2738.
Reid et al., "Improved packaging efficiency for ocular applications of AAV vectors through inclusion of miRNA recognition sequences," ARVO Annual Meeting Abstract, Jun. 2015, 2 pages.
Strobel et al., "Abstract #: 678. Increasing AAV Vector Yield by Riboswitch-Mediated Attenuation of Toxic Transgene Effects in HEK-293 Producer Cells," Molecular Therapy, 2015, 23: S269-S270.
Wang et al., "An shRNA silencing a non-toxic transgene reduces nutrient consumption and increases production of adenoviral vectors in a novel packaging cell," Journal of Cellular Physiology, May 2009, 219 365-371.
SG Search Report in Singapore Appln. No. 11201803353P, dated Jul. 8, 2019, 8 pages.

\* cited by examiner

INTRATHECAL DELIVERY OF NUCLEIC ACID SEQUENCES ENCODING ABCD1 FOR TREATMENT OF ADRENOMYELONEUROPATHY

RELATED APPLICATIONS

This application is a continuation of U.S. patent application Ser. No. 15/773,337, filed May 3, 2018, which is a § 371 National Stage Application of PCT/US2016/060375, filed Nov. 3, 2016, which claims the benefit of U.S. Provisional Application No. 62/300,691, filed Feb. 26, 2016, and U.S. Provisional Application No. 62/251,208, filed Nov. 5, 2015. The entire disclosures of the aforementioned applications are incorporated herein by reference.

FEDERALLY SPONSORED RESEARCH OR DEVELOPMENT

This work was supported by Grant Nos. NS081374 and NS072446 awarded by the National Institutes of Health. The government has certain rights in the invention.

BACKGROUND OF THE INVENTION

X-linked adrenoleukodystrophy (X-ALD), a progressive genetic disorder, is caused by mutations in the ABCD1 gene, which encodes a peroxisomal ATP-binding cassette transporter (ABCD1) responsible for transport of CoA-activated very long-chain fatty acids (VLCFA) into the peroxisome for degradation leading to the accumulation of high levels of saturated, very long chain fatty acids (VLCFA) in plasma and tissues of the brain and adrenal cortex. Symptoms can begin in childhood or adulthood. Adult ALD patients typically develop adrenomyeloneuropathy (AMN), a debilitating neurological disorder, in their twenties (Engelen et al., Orphanet J Rare Dis. 2012; 7: 51). The Abcd1$^{-/-}$ mouse develops a phenotype similar to AMN, manifesting spinal cord axon degeneration as well as peripheral neuropathy due to affected dorsal root ganglion neurons (DRGs) (Pujol et al., Hum Mol Genet. 2002; 11:499-505). Transduction of central nervous system cells in vitro and in vivo using recombinant adeno-associated virus serotype 9 (rAAV9) vector for delivery of the human ABCD1 gene was previously reported. Unfortunately, intravenous delivery in young mice is associated with cardiac toxicity due to transgene overexpression. Delivery systems that provide non-toxic levels of ABCD1 in patients suffering from X-ALD or AMN would be highly desirable.

SUMMARY OF THE INVENTION

Other features and advantages of the invention will be apparent from the Detailed Description, and from the claims. Thus, other aspects of the invention are described in the following disclosure and are within the ambit of the invention.

In one aspect, the invention provides a method of increasing adeno-associated Virus 9 (AAV9) vector titers in transfected producer cells grown in culture, said method comprising the steps of i) incubating a nucleic acid sequence that is complementary to an mRNA encoding ATP binding cassette subfamily D member 1 (ABCD1) with the cells and ii) transfecting an AAV9 vector comprising a nucleotide sequence encoding ABCD1 into the cells (AAV9-ABCD1 vector), wherein the amount of ABCD1 mRNA expressed from the AAV9 vector is decreased, thereby increasing AAV9-ABCD1 vector yield in cell lysate and/or media by about 1 fold to about 50 fold compared to a reference standard.

In one embodiment, the nucleic acid sequence that is complementary to an mRNA encoding ABCD1 is an interfering RNA.

In another embodiment, the interfering RNA is an shRNA or siRNA.

In yet another embodiment, the siRNA comprises SEQ ID NO. 4, SEQ ID NO. 5, SEQ ID NO. 6, SEQ ID NO. 7 or a combination thereof.

In yet another embodiment, the reference standard comprises AAV9-ABCD1 vector yield in cell lysate and/or media from producer cells that were not incubated with a nucleic acid sequence that is complementary to an mRNA encoding ABCD1.

In yet another aspect, the invention provides a method of treating X-linked adrenoleukodystrophy (X-ALD) in a subject in need thereof comprising administering to the subject a composition comprising purified AAV9-ABCD1 vector obtained from the producer cells having increased AAV9 vector titers compared to a reference standard.

In one embodiment, the composition comprising purified AAV9-ABCD1 vector is administered to the subject by intrathecal administration.

In yet another aspect, the invention provides a method of treating X-linked adrenoleukodystrophy (X-ALD) in a subject in need thereof comprising administering to the subject an adeno-associated Virus (AAV) vector encoding an ATP binding cassette subfamily D member 1 (ABCD1), wherein said vector is administered to the subject by intrathecal administration.

In one embodiment, the intrathecal administration is mediated by an osmotic pump.

In another embodiment, the dose of vector is $0.5 \times 10^{11}$ GC.

In yet another embodiment, the AAV is AAV9.

In yet another aspect, the invention provides a method of providing ATP binding cassette subfamily D member 1 (ABCD1) to a subject having X-linked adrenoleukodystrophy (X-ALD) comprising administering to the subject a vector encoding ABCD1, wherein said vector is administered to the subject by intrathecal administration, and wherein ABCD1 expression from said vector in the central nervous system is less than ABCD1 expression from said vector in peripheral organs.

In one embodiment, the intrathecal administration is mediated by an osmotic pump.

In another embodiment, the dose of vector is about $1 \times 10^{13}$ GC to about $10 \times 10^{13}$ GC.

In yet another embodiment, the vector is an adeno-associated virus (AAV) vector.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

BRIEF DESCRIPTION OF THE DRAWINGS

The following Detailed Description, given by way of example, but not intended to limit the invention to certain embodiments described, may be understood in conjunction with the accompanying figures, incorporated herein by reference.

DETAILED DESCRIPTION OF THE INVENTION

Definitions

Figure 1:
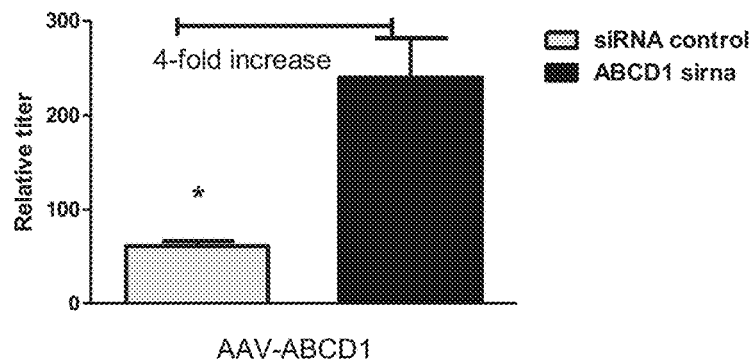
FIG. 1 depicts improved AAV9-ABCD1 vector titers from transfected 293T cells incubated with siRNA specific for ABCD1 mRNA.

Unless otherwise defined, all technical and scientific terms used herein have the same meaning as commonly understood by one of ordinary skill in the art to which this invention belongs. In case of conflict, the present application, including definitions will control.

A "subject" is a vertebrate, including any member of the class mammalia, including humans, domestic and farm animals, and zoo, sports or pet animals, such as mouse, rabbit, pig, sheep, goat, cattle and higher primates.

As used herein, the terms "treat," "treating," "treatment," and the like refer to reducing or ameliorating X-ALD, e.g., adrenomyeloneuropathy (AMN), and/or symptoms associated therewith. It will be appreciated that, although not precluded, treating X-ALD or AMN does not require that the disorder, condition or symptoms associated therewith be completely eliminated.

Unless specifically stated or clear from context, as used herein, the term "about" is understood as within a range of normal tolerance in the art, for example within 2 standard deviations of the mean. "About" is understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

As used herein "a decrease in expression" refers to an amount of ABCD1 gene expression or protein expression in peripheral organs of a subject that is at least about 0.05 fold less (for example 0.1, 0.2, 0.3, 0.4, 0.5, 1, 5, 10, 25, 50, 100, 1000, 10,000-fold or more less) than the amount of ABCD1 gene expression or protein expression in the central nervous system of a subject having been administered a vector encoding ABCD1 according to the methods described herein. "Decreased" as it refers to ABCD1 gene expression or protein expression in peripheral organs of a subject also means at least about 5% less (for example 5, 6, 7, 8, 9, 10, 15, 20, 25, 30, 35, 40, 45, 50, 55, 60, 65, 70, 75, 80, 85, 90, 95, 99 or 100%) than the amount of ABCD1 gene expression or protein expression in the central nervous system of a subject having been administered a vector encoding ABCD1 according to the methods described herein. Amounts can be measured according to standard methods known in the art for determining amounts of gene expression or protein expression.

As used herein "an increase in vector titers" refers to an amount of titer from producer cells transfected with a vector encoding ABCD1 that is at least about 0.05 fold more (for example 0.1, 0.2, 0.3, 0.4, 0.5, 1, 5, 10, 25, 50, 100, 1000, 10,000-fold or more) than the amount of titer from producer cells that were not incubated with a nucleic acid sequence that is complementary to an mRNA encoding ABCD1 according to the methods described herein. "Increased" as it refers to an amount of titer (concentration of AAV vector, often described in genome copies per milliliter) from producer cells transfected with a vector encoding ABCD1 also means at least about 5% more (for example 5, 6, 7, 8, 9, 10, 15, 20, 25, 30, 35, 40, 45, 50, 55, 60, 65, 70, 75, 80, 85, 90, 95, 99 or 100%) than the amount of titer from producer cells that were not incubated with a nucleic acid sequence that is complementary to an mRNA encoding ABCD1 according to the methods described herein. Amounts can be measured according to standard methods known in the art for determining amounts of AAV genomes, transgene expression, or protein expression.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (as well as fractions thereof unless the context clearly dictates otherwise).

As used herein, the term "reference level" refers to the level of titer in a known sample against which another test sample is compared. A reference level can be obtained, for example, from producer cells that were not incubated with a nucleic acid sequence that is complementary to an mRNA encoding ABCD1 or with a control antisense oligonucleotide or siRNA. A reference level can be obtained, for example, from untreated subjects that do not have X-ALD. "Untreated" refers to the lack of therapy from administration of a vector expressing an ABCD1 transgene.

In this disclosure, "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

Other definitions appear in context throughout this disclosure.

Compositions and Methods

Compositions and methods of the invention provide treatments for X-linked adrenoleukodystrophy (X-ALD). X-linked adrenoleukodystrophy is a genetic disorder, caused by mutations in the ABCD1 gene, that occurs primarily in males and mainly affects the nervous system and the adrenal glands. Myelin of the brain and spinal cord deteriorate (demyelination), which reduces the functional ability of the nerves. In addition, damage to the outer layer of the adrenal glands (adrenal cortex) causes a shortage of certain hormones (adrenocortical insufficiency). There are several distinct types of X-linked adrenoleukodystrophy, including a childhood cerebral form, an adrenomyeloneuropathy (AMN) type, and a form called Addison disease. As used herein, X-ALD does not include "neonatal adrenoleukodystrophy," which belongs to the peroxisomal biogenesis disorders of the Zellweger spectrum and is unrelated to mutations in ABCD1. Methods for diagnosing or identifying subjects with X-ALD or AMN are known in the art and can include measurement of plasma very long chain fatty acid (VLCFA) levels and/or genetic testing; see, e.g., Engelen et al., Orphanet J Rare Dis. 2012; 7: 51; Aubourg and Chaussain, Horm Res. 2003; 59 Suppl 1:104-5; Steinberg et al., Curr Protoc Hum Genet. 2008 Chapter 17:Unit 17.6; Steinberg S J, Moser A B, Raymond G V. X-Linked Adrenoleukodystrophy. 1999 Mar. 26 [Updated 2015 Apr. 9]. In: Pagon R A, Adam M P, Ardinger H H, et al., editors. GeneReviews® [Internet]. Seattle (Wash.): University of Washington, Seattle; 1993-2016. Available from: ncbi.nlm.nih.gov/books/NBK1315/).

Mutations in the ABCD1 gene cause X-linked adrenoleukodystrophy. The ABCD1 gene encodes the adrenoleukodystrophy protein (ALDP), which is involved in transporting very long-chain fatty acids (VLCFAs) into peroxisomes. ABCD1 gene mutations result in a deficiency of ALDP. When this protein is lacking, the transport and subsequent breakdown of VLCFAs is disrupted, causing abnormally high levels of these fats in the body. The accumulation of VLCFAs may be toxic to the adrenal cortex and myelin.

Correction of the genetic defect by gene therapy presents a viable therapy. Targeted, specific delivery of the ABCD1 gene to the CNS is essential to avoid toxicity in peripheral organs. This can be achieved, for example, by administering an adeno-associated virus (AAV) vector encoding ABCD1 via intrathecal administration.

Sequences encoding the ABCD1 cDNA and its expressed protein are well known, and can be found, for example at Genbank Accession Nos. NG_009022.2 and NP_000024.2.

"AAV" is adeno-associated virus, and may be used to refer to the recombinant virus vector itself or derivatives thereof. The term covers all subtypes, serotypes and pseudotypes, and both naturally occurring and recombinant forms, except where required otherwise. As used herein, the term "serotype" refers to an AAV which is identified by and distinguished from other AAVs based on its serology, e.g., there are eleven serotypes of AAVs, AAV1-AAV11, and the term encompasses pseudotypes with the same properties. Many of these serotypes have unique biological properties from other AAV serotypes (e.g. cell surface receptor binding, intracellular trafficking). Thus, for example, AAV5 serotypes include AAV with the biological properties of AAV5, e.g., a pseudotyped AAV comprising AAV5 capsid and an AAV genome which is not derived or obtained from AAV5 or which genome is chimeric.

An "AAV vector" refers to a viral particle composed of at least one AAV capsid protein and an encapsidated polynucleotide. If the particle comprises a heterologous polynucleotide (i.e., a polynucleotide other than a wild-type AAV genome such as a transgene to be delivered to a mammalian cell), it can be referred to as "rAAV (recombinant AAV)." An AAV "capsid protein" includes a capsid protein of a wild-type AAV, as well as modified forms of an AAV capsid protein which are structurally and or functionally capable of packaging an AAV genome and bind to at least one specific cellular receptor which may be different than a receptor employed by wild type AAV. A modified AAV capsid protein includes a chimeric AAV capsid protein such as one having amino acid sequences from two or more serotypes of AAV, e.g., a capsid protein formed from a portion of the capsid protein from AAV5 fused or linked to a portion of the capsid protein from AAV2, and a AAV capsid protein having a tag or other detectable non-AAV capsid peptide or protein fused or linked to the AAV capsid protein, e.g., a portion of an antibody molecule which binds the transferrin receptor may be recombinantly fused to the AAV-2 capsid protein.

Cells capable of producing AAV are known in the art and include, but are not limited to 293 cells, HeLa cells and insect cells.

In certain embodiments, methods of producing high titers of AAV can be utilized to maximize administration of ABCD1. Transfected producer cells grown in culture can be incubated with a nucleic acid sequence that is complementary to an mRNA encoding ATP binding cassette subfamily D member 1 (ABCD1) and ii) transfected with an AAV vector comprising a nucleotide sequence encoding ABCD1 into the cells (e.g., AAV9-ABCD1 vector). The amount of ABCD1 mRNA expressed from the AAV vector is decreased, thereby increasing AAV-ABCD1 vector yield in cell lysate and/or media by about 1 fold to about 50 fold compared to a reference standard. In certain embodiments, the AAV-ABCD1 vector yield in cell lysate and/or media is increased by about 4 fold. Vector titers can be determined according to methods well known in the art. Typically, this is performed using dot blots or quantitative PCR to measure AAV genomes. In general, AAV vector yields can be about $1 \times 10^{10}$ genome copies/ml (gc/ml) to about $1 \times 10^{16}$ gc/ml from cell lysates and from media.

In specific embodiments, the reference standard comprises AAV-ABCD1 vector yield in cell lysate and/or media from producer cells that were not incubated with a nucleic acid sequence that is complementary to an mRNA encoding ABCD1.

This can be achieved, for example, by providing an antisense oligonucleotide that is complementary to ABCD1 mRNA. Other nucleic acid sequences for use in practicing the methods of the invention and that are complementary to ABCD1 mRNA can be those which inhibit post-transcriptional processing of ABCD1, such as an interfering RNA, including but not limited to an shRNA or siRNA, or an antagomir.

Sequences encoding the ABCD1 mRNA are well known, and can be found, for example at Genbank Accession Nos. NM_000033.3.

Antisense oligonucleotides are typically designed to block expression of a DNA or RNA target by binding to the target and halting expression at the level of transcription, translation, or splicing. Antisense oligonucleotides of the present invention are complementary nucleic acid sequences designed to hybridize under stringent conditions to ABCD1 mRNA. Thus, oligonucleotides are chosen which are sufficiently complementary to the target, i.e., hybridize sufficiently well and with sufficient specificity, to give the desired effect.

In the context of this invention, hybridization means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. Complementary, as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target.

It is understood in the art that a complementary nucleic acid sequence need not be 100% complementary to that of its target nucleic acid to be specifically hybridizable. A complementary nucleic acid sequence of the invention is specifically hybridizable when binding of the sequence to the target DNA or RNA molecule interferes with the normal function of the target DNA or RNA to cause a loss of activity, and there is a sufficient degree of complementarity to avoid non-specific binding of the sequence to non-target sequences under conditions in which specific binding is desired, i.e., under physiological conditions in the case of in vivo assays or therapeutic treatment, and in the case of in vitro assays, under conditions in which the assays are performed under suitable conditions of stringency. For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

It is preferred that the antisense oligonucleotides of the present invention comprise at least 80% sequence complementarity to a target region within the target nucleic acid, moreover that they comprise 90% sequence complementarity and even more preferable to comprise 95% sequence complementarity to the target region within the target nucleic acid sequence to which they are targeted. For example, an antisense compound in which 18 of 20 nucleobases of the antisense oligonucleotide are complementary, and would therefore specifically hybridize, to a target region would represent 90 percent complementarity. Percent complementarity of an antisense compound with a region of a target nucleic acid can be determined routinely using basic local alignment search tools (BLAST programs) (Altschul et al., J. Mol. Biol., 1990, 215, 403-410; Zhang and Madden, Genome Res., 1997, 7, 649-656). Antisense and other compounds of the invention, which hybridize to ABCD1 mRNA, are identified through experimentation, and representative sequences of these compounds are herein below identified as preferred embodiments of the invention.

In another embodiment, the nucleic acid sequence that is complementary to ABCD1 mRNA can be an interfering RNA, including but not limited to an shRNA or siRNA. Interfering RNA includes, but is not limited to small interfering RNA ("siRNA") and small hairpin RNA ("shRNA"). Methods for constructing interfering RNAs are well known in the art. For example, the interfering RNA can be assembled from two separate oligonucleotides, where one strand is the sense strand and the other is the antisense strand, wherein the antisense and sense strands are self-complementary (i.e., each strand comprises nucleotide sequence that is complementary to nucleotide sequence in the other strand; such as where the antisense strand and sense strand form a duplex or double stranded structure); the antisense strand comprises nucleotide sequence that is complementary to a nucleotide sequence in a target nucleic acid molecule or a portion thereof (i.e., an undesired gene) and the sense strand comprises nucleotide sequence corresponding to the target nucleic acid sequence or a portion thereof. Alternatively, interfering RNA is assembled from a single oligonucleotide, where the self-complementary sense and antisense regions are linked by means of nucleic acid based or non-nucleic acid-based linker(s). The interfering RNA can be a polynucleotide with a duplex, asymmetric duplex, hairpin or asymmetric hairpin secondary structure, having self-complementary sense and antisense regions, wherein the antisense region comprises a nucleotide sequence that is complementary to nucleotide sequence in a separate target nucleic acid molecule or a portion thereof and the sense region having nucleotide sequence corresponding to the target nucleic acid sequence or a portion thereof. The interfering can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siRNA molecule capable of mediating RNA interference.

In certain embodiments of the invention, the interfering RNA coding region encodes a self-complementary RNA molecule having a sense region, an antisense region and a loop region. Such an RNA molecule when expressed desirably forms a "hairpin" structure, and is referred to herein as an "shRNA." The loop region is generally between about 2 and about 10 nucleotides in length. In a preferred embodiment, the loop region is from about 6 to about 9 nucleotides in length. In one such embodiment of the invention, the sense region and the antisense region are between about 15 and about 20 nucleotides in length. Following post-transcriptional processing, the small hairpin RNA is converted into a siRNA by a cleavage event mediated by the enzyme Dicer, which is a member of the RNase III family. The siRNA is then capable of inhibiting the expression of a gene with which it shares homology. For details, see Brummelkamp et al., Science 296:550-553, (2002); Lee et al, Nature Biotechnol., 20, 500-505, (2002); Miyagishi and Taira, Nature Biotechnol 20:497-500, (2002); Paddison et al. Genes & Dev. 16:948-958, (2002); Paul, Nature Biotechnol, 20, 505-508, (2002); Sui, Proc. Natl. Acad. Sd. USA, 99(6), 5515-5520, (2002); Yu et al. Proc Natl Acad Sci USA 99:6047-6052, (2002).

The target RNA cleavage reaction guided by siRNAs is highly sequence specific. In general, siRNA containing a nucleotide sequences identical to a portion of the target gene (i.e., ABCD1) are preferred for inhibition. However, 100% sequence identity between the siRNA and the target gene is not required to practice the present invention. Thus the invention has the advantage of being able to tolerate sequence variations that might be expected due to genetic mutation, strain polymorphism, or evolutionary divergence. For example, siRNA sequences with insertions, deletions, and single point mutations relative to the target sequence have also been found to be effective for inhibition. Alternatively, siRNA sequences with nucleotide analog substitutions or insertions can be effective for inhibition.

In yet another embodiment, the nucleic acid sequence that is complementary to ABCD1 mRNA is an antagomir. Antagomirs are single stranded, double stranded, partially double stranded and hairpin structured chemically modified oligonucleotides that target a microRNA. Preferably, an antagomir featured in the invention includes a nucleotide sequence sufficiently complementary to hybridize to a miRNA target sequence of about 10 to 25 nucleotides, preferably about 15 to 20 nucleotides.

In certain embodiments, antagomirs are RNA-like oligonucleotides that harbor various modifications for RNase protection and pharmacologic properties such as enhanced tissue and cellular uptake. An antagomir can differ from normal RNA by having complete 2'-O-methylation of sugar, phosphorothioate backbone and a cholesterol-moiety at 3'-end. Phosphorothioate modifications provide protection against RNase activity and their lipophilicity contributes to enhanced tissue uptake. In a preferred embodiment, the antagomir includes six phosphorothioate backbone modifications; two phosphorothioates are located at the 5'-end and four at the 3'-end. Antagomirs of the present invention can also be modified with respect to their length or otherwise the number of nucleotides making up the antagomir.

The nucleic acid sequences used to practice this invention, whether RNA, cDNA, genomic DNA, vectors, viruses or hybrids thereof, can be isolated from a variety of sources, genetically engineered, amplified, and/or expressed/generated recombinantly. Recombinant nucleic acid sequences can be individually isolated or cloned and tested for a desired activity. Any recombinant expression system can be used, including e.g. in vitro, bacterial, fungal, mammalian, yeast, insect or plant cell expression systems.

Nucleic acid sequences of the invention can be inserted into delivery vectors and expressed from transcription units within the vectors (e.g., AAV vectors). The recombinant vectors can be DNA plasmids or viral vectors. Generation of the vector construct can be accomplished using any suitable genetic engineering techniques well known in the art, including, without limitation, the standard techniques of PCR, oligonucleotide synthesis, restriction endonuclease digestion, ligation, transformation, plasmid purification, and DNA sequencing, for example as described in Sambrook et al. Molecular Cloning: A Laboratory Manual. (1989)), Coffin et al. (Retroviruses. (1997)) and "RNA Viruses: A Practical Approach" (Alan J. Cann, Ed., Oxford University Press, (2000)). As will be apparent to one of ordinary skill in the art, a variety of suitable vectors are available for transferring nucleic acids of the invention into cells. The selection of an appropriate vector to deliver nucleic acids and optimization of the conditions for insertion of the selected expression vector into the cell, are within the scope of one of ordinary skill in the art without the need for undue experimentation. Viral vectors comprise a nucleotide sequence having sequences for the production of recombinant virus in a packaging cell. Viral vectors expressing nucleic acids of the invention can be constructed based on viral backbones including, but not limited to, a retrovirus, lentivirus, adenovirus, adeno-associated virus, pox virus or alphavirus. The recombinant vectors capable of expressing the nucleic acids of the invention can be delivered as described herein, and persist in target cells (e.g., stable transformants).

Nucleic acid sequences used to practice this invention can be synthesized in vitro by well-known chemical synthesis techniques, as described in, e.g., Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896;

Narang (1979) Meth. Enzymol. 68:90; Brown (1979) Meth. Enzymol. 68:109; Beaucage (1981) Tetra. Lett. 22:1859; U.S. Pat. No. 4,458,066.

Nucleic acid sequences of the invention can be stabilized against nucleolytic degradation such as by the incorporation of a modification, e.g., a nucleotide modification. For example, nucleic acid sequences of the invention include a phosphorothioate at least the first, second, or third internucleotide linkage at the 5' or 3' end of the nucleotide sequence. As another example, the nucleic acid sequence can include a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O—NMA). As another example, the nucleic acid sequence can include at least one 2'-O-methyl-modified nucleotide, and in some embodiments, all of the nucleotides include a 2'-O-methyl modification.

Techniques for the manipulation of nucleic acids used to practice this invention, such as, e.g., subcloning, labeling probes (e.g., random-primer labeling using Klenow polymerase, nick translation, amplification), sequencing, hybridization and the like are well described in the scientific and patent literature, see, e.g., Sambrook, ed., MOLECULAR CLONING: A LABORATORY MANUAL (2ND ED.), Vols. 1-3, Cold Spring Harbor Laboratory, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y. (1993).

ABCD1 vector administration provided by intravenous (IV) or intracerebroventricular (ICV) administration has recently been determined to cause cardiac toxicity. Intrathecal administration is a route of administration comprising injection of desired agents into the subarachnoid space of the spinal canal, thereby providing the agents into the cerebrospinal fluid (CSF). Using intrathecal administration, ABCD1 expression from a vector within in the central nervous system is less than ABCD1 expression from a vector within peripheral organs, such as the heart. Excess ABCD1 expression in peripheral organs can result in toxicity and therefore, intrathecal administration of ABCD1 vectors comprises an improved method of therapy for X-ALD, e.g., for AMN.

In some embodiments, the intrathecal administration is via a pump. The pump may be a surgically implanted osmotic pump. In certain embodiments, the osmotic pump is implanted into the subarachnoid space of the spinal canal to facilitate intrathecal administration.

In certain embodiments, human subjects receive a one-time treatment of intrathecally delivered vector (e.g., AAV9) comprising ABCD1 in an amount of about $1 \times 10^{13}$ GC to about $10 \times 10^{13}$ GC over a period of about 24 hours.

The slow continuous intrathecal infusion of the AAV9-hABCD1 can be scaled up to humans by using an osmotically driven pump such as the DUROS® implant, ALZA Corporation (Mountain View, Calif.). See also, J. C. Wright, J. Culwell, Long-term controlled delivery of therapeutic agents by the osmotically driven DUROS® implant, in: M. J. Rathbone, J. Hadgraft, M. S. Roberts (Eds.), Modified-Release Drug Delivery Technology, Informa Healthcare, New York, 2008, pp. 143-149.

Osmotic delivery devices and their component parts have been described, for example, in U.S. Pat. Nos. 5,609,885; 5,728,396; 5,985,305; 5,997,527; 6,113,938; 6,132,420; 6,156,331; 6,217,906; 6,261,584; 6,270,787; 6,287,295; 6,375,978; 6,395,292; 6,508,808; 6,544,252; 6,635,268; 6,682,522; 6,923,800; 6,939,556; 6,976,981; 6,997,922; 7,014,636; 7,207,982; 7,112,335; 7,163,688; U.S. Patent Publication Nos. 2005-0175701, 2007-0281024, and 2008-0091176.

The DUROS® delivery device typically consists of a cylindrical reservoir which contains the osmotic engine, piston, and drug formulation. The reservoir is capped at one end by a controlled-rate water-permeable membrane and capped at the other end by a diffusion moderator through which drug formulation is released from the drug reservoir. The piston separates the drug formulation from the osmotic engine and utilizes a seal to prevent the water in the osmotic engine compartment from entering the drug reservoir. The diffusion moderator is designed, in conjunction with the drug formulation, to prevent body fluid from entering the drug reservoir through the orifice.

The DUROS® device releases a therapeutic agent at a predetermined rate based on the principle of osmosis. Extracellular fluid enters the DUROS® device through a semipermeable membrane directly into a salt engine that expands to drive the piston at a slow and even delivery rate. Movement of the piston forces the drug formulation to be released through the orifice or exit port at a predetermined sheer rate. In one embodiment of the present invention, the reservoir of the DUROS® device is load with a suspension formulation of the present invention, comprising, for example, $1 \times 10^{11}$ gc AAV9-hABCD1, wherein the device is capable of delivering the suspension formulation to a subject over an extended period of time at a pre-determined, therapeutically effective delivery rate.

Other implantable, drug delivery devices may be used in the practice of the present invention and may include regulator-type implantable pumps that provide constant flow, adjustable flow, or programmable flow of the compound, such as those available from Codman & Shurtleff, Inc. (Raynham, Mass.), Medtronic, Inc. (Minneapolis, Minn.), and Tricumed Medinzintechnik GmbH (Germany).

The present invention is additionally described by way of the following illustrative, non-limiting Examples that provide a better understanding of the present invention and of its many advantages.

EXAMPLES

The following Examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following Examples do not in any way limit the invention.

Example 1: Production of AAV9-ABCD1 in the Presence of siRNA Specific for ABCD1 mRNA Improves AAV Vector Titers from Transfected 293T Cells A high amount of cell death/cytopathic effects during production of AAV9-ABCD1 has been previously observed, likely due to overexpression of ABCD1 protein in producer cells. This toxicity reduced AAV vector yields. To mitigate the toxicity and improve vector yields, ABCD1 mRNA was targeted using a pool of siRNAs.

AAV packing was carried out as follows. $1-1.5 \times 10^7$ 293 T cells were plated on 15 cm plates in and cultured overnight.

TABLE 1

Packaging and Collection Media

DMEM High Glucose, HEPES
DMEM 10% FBS 1% p/s
DMEM 2% FBS 1% p/s
2.5 mM Hepes buffer
2M CaCl
2x Hebs buffer, pH 7.04-7.047
PBS
Trypsin
NaCl, 50 mM HEPES, 1.5 mM
Na2HPO4
5 mM EDTA On day 2, transfection mix was prepared as follows:

TABLE 2

Transfection Mix

| Tube A | Tube B |
|---|---|
| Vector Construct 10 ug | 2x Hebs 780 ul |
| Adenovirus helper 26 ug | |
| **Serotype plasmid 12 ug | |
| 2M CaCl 96.9 | |
| 2.5 mM Hepes up to 780 ul | |
| Total Volume 780 ul | Total Volume 780 ul |

Tube A and Tube B were combined drop-wise while vortexing for 1 minute. The mix was incubated at room temperature for 20 minutes. 1.5 ml of virus mix per 15 cm plate was added, distributing drop-wise over the surface of the plate. Plates were tilted to mix evenly and incubated overnight. At day 3, media was replaced with DMEM 2% FBS 1% p/s. At day 5, half of the plate media volume was removed from each plate. Cells were collected from plates by washing with remaining media or gently using a cell scraper. Cells were spun down at 1300 RPM for 5 minutes. Supernatant was removed. Cells were loosened by flicking the bottom of the tube and re-suspended in 1 ml EDTA PBS per plate of cells and spun at 1300 RPM for 5 minutes. Cells were re-suspended in 1 ml lysis buffer per plate and optionally stored at −80 C. Following gradient purification, virus was buffer exchanged into PBS, quantified by qPCR, and used for experimentation.

On the day of 293T cell plating, cells were transfected with the pool of siRNA specific for ABCD1 mRNA or a non-targeting control siRNA. Another control was an AAV9 vector encoding GFP (AAV9-GFP) in the presence of the ABCD1 siRNA. The following day both samples were transfected with AAV plasmids to produce AAV9-ABCD1.

The siRNA protocol has multiple steps:
1. Prepare 5 μM of pooled (25% of each of 4 siRNAs) siRNA solution in 1× siRNA buffer (GE Healthcare) or another appropriate RNase-free solution from stock solution.
2. In separate tubes, dilute the siRNA (100 ul in tube1) and the appropriate DharmaFECT transfection reagent (30 ul in tube2) with serum-free DMEM medium to 2 ml volume respectively.
3. Gently mix the contents of each tube by pipetting carefully up and down. Incubate for 5 minutes at room temperature.
4. Add the contents of Tube 1 to Tube 2, for a total volume of 4 ml. Mix by pipetting carefully up and down and incubate for 20 minutes at room temperature. Add 12 ml of complete DMEM (10% FBS) to the 4 ml.
5. Add 4 ml of resuspended 293T cells in complete media that are at a concentration of 3.75e6 cells/ml (total 1.5E7 cells) to the 16 ml of the transfection mixture from step 4 (final siRNA concentration of 25 nM).
6. Plate into 15 cm dish and incubate 24 h.
7. Change media to complete DMEM 10% FBS 1 h before calcium phosphate transfection with AAV plasmids.
8. Proceed with standard AAV production and purification protocol.

Three days post transfection cells were harvested, lysed, and vector yields (in genome copies) was determined by qPCR as follows:

TABLE 3 qPCR Materials

F2: CCTCGACTGTGCCTTCTAG (SEQ ID NO. 1)

R2: TGCGATGCAATTTCCTCAT (SEQ ID NO. 2)

Probe: 5'FAM-tgccagccatctgttgtttgcc-MGB
(SEQ ID NO. 3)

Nuclease free water

F and R qPCR primers

TM FAM Probe

TaqMan Fast universal PCR Master Mix

PCR plates for 7500 (Fast) Qpcr

PCR plate film

The qPCR protocol has multiple steps:
1. Dilute vector 1:100-1:1000 in nuclease-free water and vortex. Use in qPCR.
2. Use plasmid 675.5 (5999 bp) as genome copy (GC) standard. Create a standard from $10^1$-$10^2$ gc/mL.
3. Prepare the master mix in an amount large enough to measure the standards and samples in triplicate. The master mix includes 2 ul H2O, 1.2 ul primer mix (F and R=5 ul of each 100 um stock in 90 ul of water), 1 ul primer mix (F and R=6 ul of each 100 um stock in 88 ul of water), 0.8 ul TM FAM Probe 2.5 uM, 1 ul TM FAM Probe 2 uM (4 ul of 100 uM stock+196 ul water), and 5 ul of TaqMan Fast universal PCR Master Mix 2×.
4. Mix and aliquot 9 ul in wells of plate.
5. Add 1 ul of template diluted in water.
6. Program 7500 machine to have thermal cycling parameters where stage 1 has reps 1, 95° C.:20 and stage 2 has reps 40, 95° C.:03; 60° C.:30.
7. Analyze data. Slope for standard should be ∼−3.3.

The yield is reported as relative titer in which the AAV9-GFP sample was set arbitrarily at 100% and the other two samples normalized to this value. Production of AAV9-ABCD1 in the presence of the siRNA pool against ABCD1 mRNA improved the vector titer (and yield) by approximately 4-fold compared to the control siRNA (FIG. 1).

TABLE 4

| siRNAs Targeting ABCD1 | |
| --- | --- |
| SEQ ID NO. 4 | CGGAUCAUGUCGUCGUACA |
| SEQ ID NO. 5 | CGGAGGAGAUCGCCUUCUA |
| SEQ ID NO. 6 | GUUCAGCGCUGUCACUUCA |
| SEQ ID NO. 7 | GAACGCCUGUGGUAUGUUA |

Figure 2:
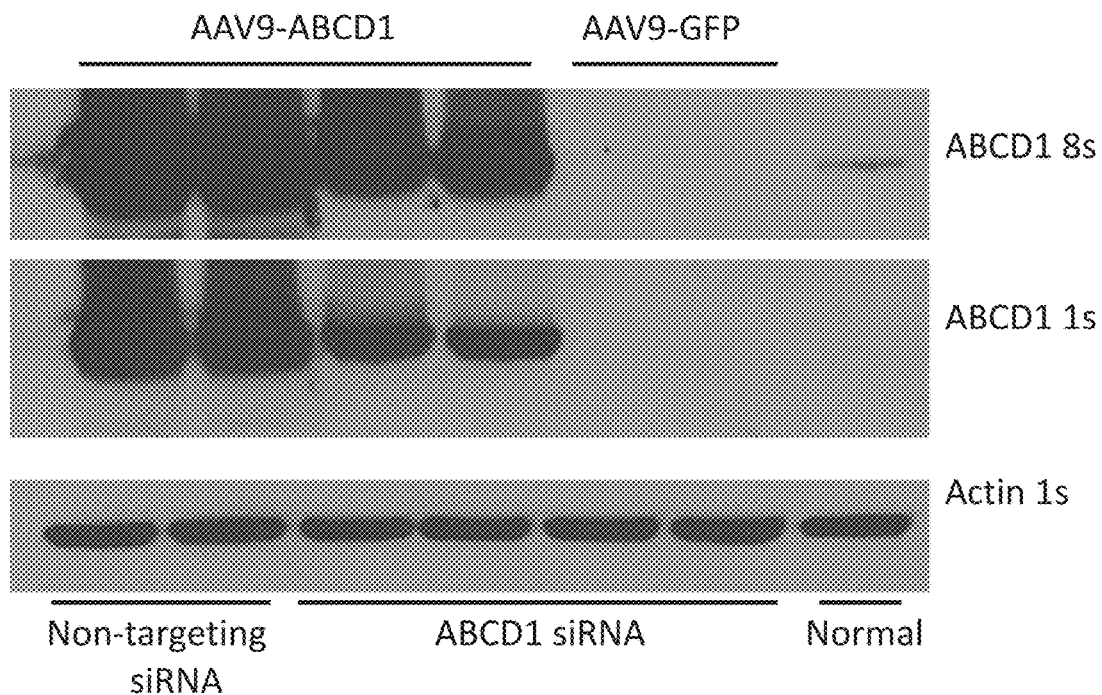
FIG. 2 depicts reduced ABCD1 protein in AAV-ABCD1 transfected cells incubated with an siRNA pool specific for ABCD1 mRNA.

293T cells were transfected with control siRNA (FIG. 2, lanes 1, 2), siRNA pool against ABCD1 mRNA (FIG. 2, lanes 3-6) or untransfected (FIG. 2, lane 7, "normal" refers to endogenous levels of ABCD1 protein in 293T cells). AAV-ABCD1 plasmid (FIG. 2, lanes 1-4) or AAV-GFP plasmid (FIG. 2, lane 5, 6) was transfected the following day. Three days later, cell lysates were electrophoresed on an SDS PAGE gel and an immunoblot for ABCD1 protein was performed to assess siRNA knockdown. Actin blotting was performed for loading control. 8 s and 1 s refers to 8 second and 1 second exposure of the radiographic film, respectively. The ABCD1 siRNA reduces the level of overexpressed ABCD1 compared to control siRNA.

Figure 3:
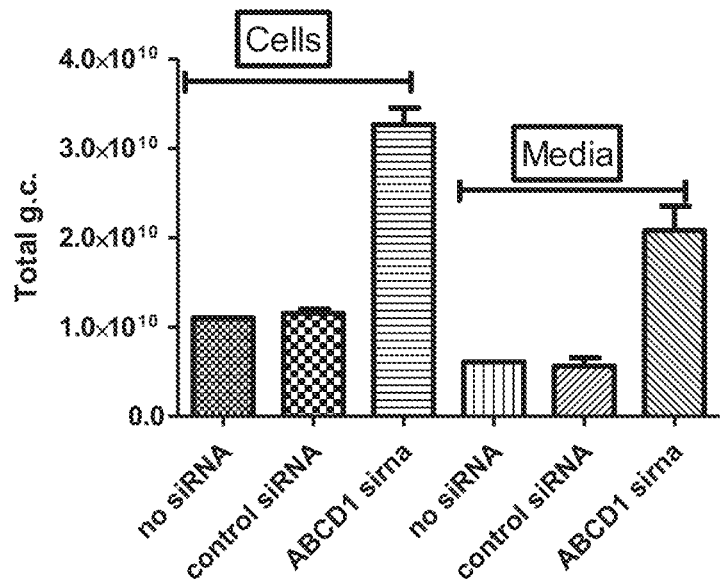
FIG. 3 depicts improved AAV9-ABCD1 vector titers from transfected 293T cells incubated with siRNA specific for ABCD1 mRNA in both cell lysates and conditioned media.

293T cells were left untransfected (no siRNA) or transfected with control siRNA or the siRNA pool against ABCD1 mRNA. The following day cells were transfected with AAV plasmids to produce AAV9-ABCD1. On day 3 post transfection of AAV plasmids, qPCR was performed to determine the amount of vector (g.c.) in cell lysate and in the media of the transfected cells. An approximate 3-4 fold increase in AAV9-ABCD1 vector yield in both cell lysate and media was observed (FIG. 3).

Example 2: Intrathecal Delivery of rAAV9-ABCD1 by Osmotic Pump in a Mouse Model of Adrenomyeloneuropathy Leads to More Uniform and Widespread Gene Delivery to the CNS Self-complementary AAV9 GFP(scAAV9GFP) and rAAV9 encoding ABCD1 (rAAV9-ABCD1) were delivered to Abcd1−/− mice intrathecally (IT) either by bolus over a 2 minute duration or by osmotic pump over 24 hour duration with PBS injection as sham control. Two weeks after injection, mice were sacrificed and perfused with 4% PFA. Tissues were then collected, sectioned and stained for immunofluorescence analysis.

scAAV9-GFP delivered IT by osmotic pump led to widespread expression across CNS-relevant cell types and DRGs in a dose-dependent manner. Spinal cord and DRG had higher expression compared with brain, but GFP expression was also detected in peripheral organs (liver, heart and adrenal gland), with highest expression seen at $3\times10^{11}$ GC.

Figure 4:
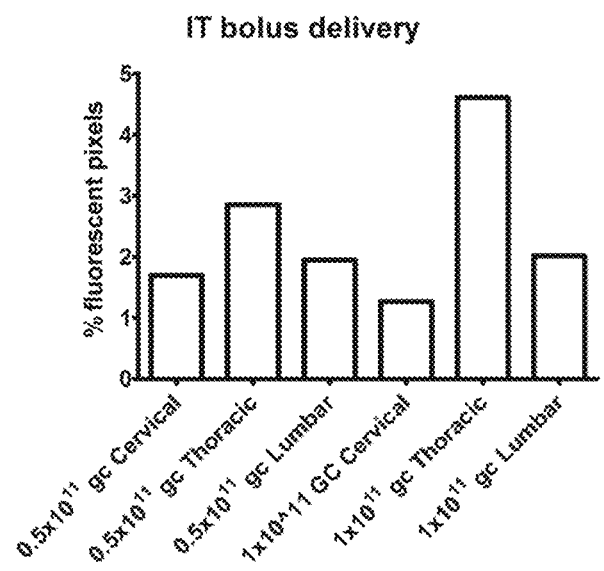
FIG. 4 depicts distribution of rAAV9-ABCD1 following intrathecal bolus delivery over 2 minutes.

A similar distribution pattern of ABCD1 protein was detected after rAAV9-ABCD1 intrathecal pump delivery. In general, higher doses ($2\times10^{11}$ GC and $1\times10^{11}$ GC) led to more expression in CNS and peripheral organs compared with a lower dose ($0.5\times10^{11}$ GC). By comparison, intrathecal bolus delivery over 2 minutes led to the highest amount of ABCD1 expression in the thoracic region, however, even a higher dose ($1\times10^{11}$ gc) did not lead to more widespread delivery in cervical and lumbar regions (FIG. 4).

Figure 5:
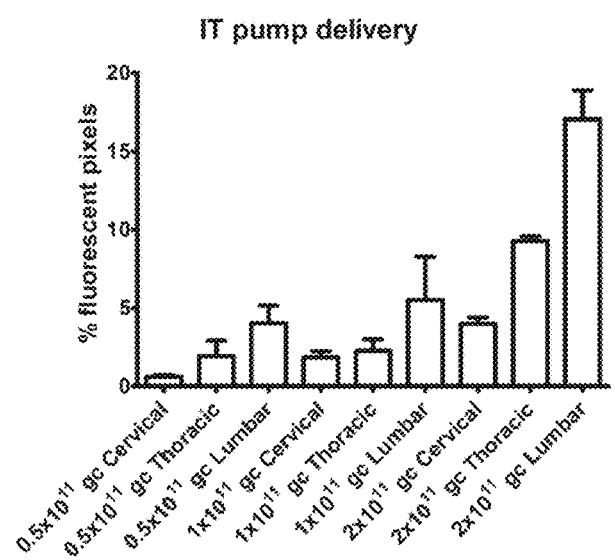
FIG. 5 depicts distribution of rAAV9-ABCD1 following intrathecal pump infusion of rAAV9-ABCD1 over 24 hours.
Figure 6:
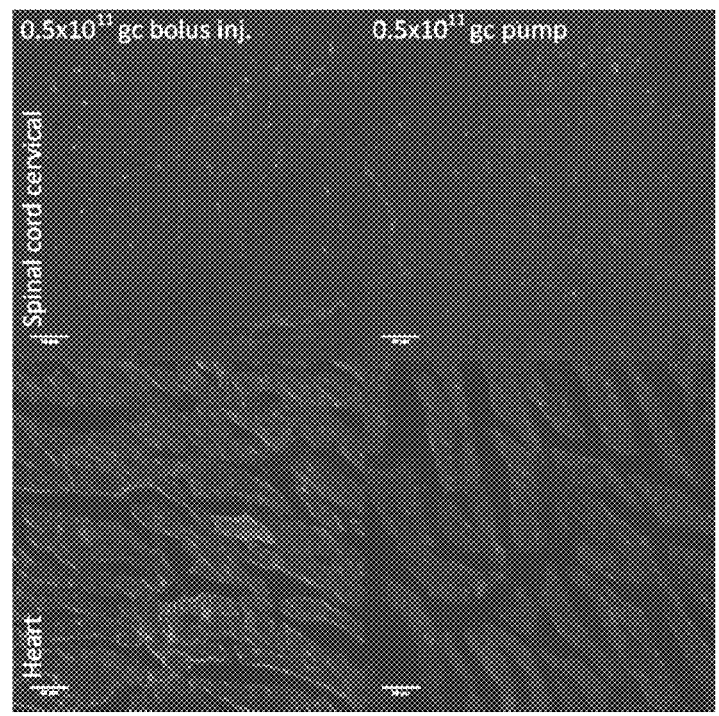
FIG. 6 depicts low dose ($0.5 \times 10^{11}$ gc) bolus and pump delivery of AAV9-ABCD1.
Figure 7:
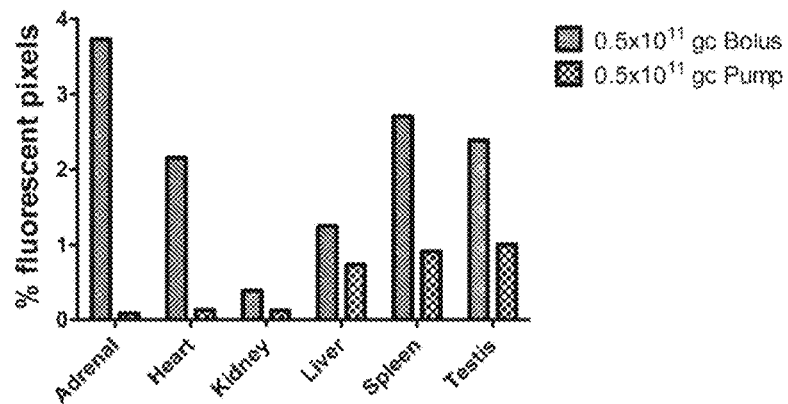
FIG. 7 depicts higher expression of ABCD1 across peripheral organs (outside the CNS) two weeks after bolus injection of AAV9-ABCD1 compared to pump infusion of AAV9-ABCD1.
Figure 8:
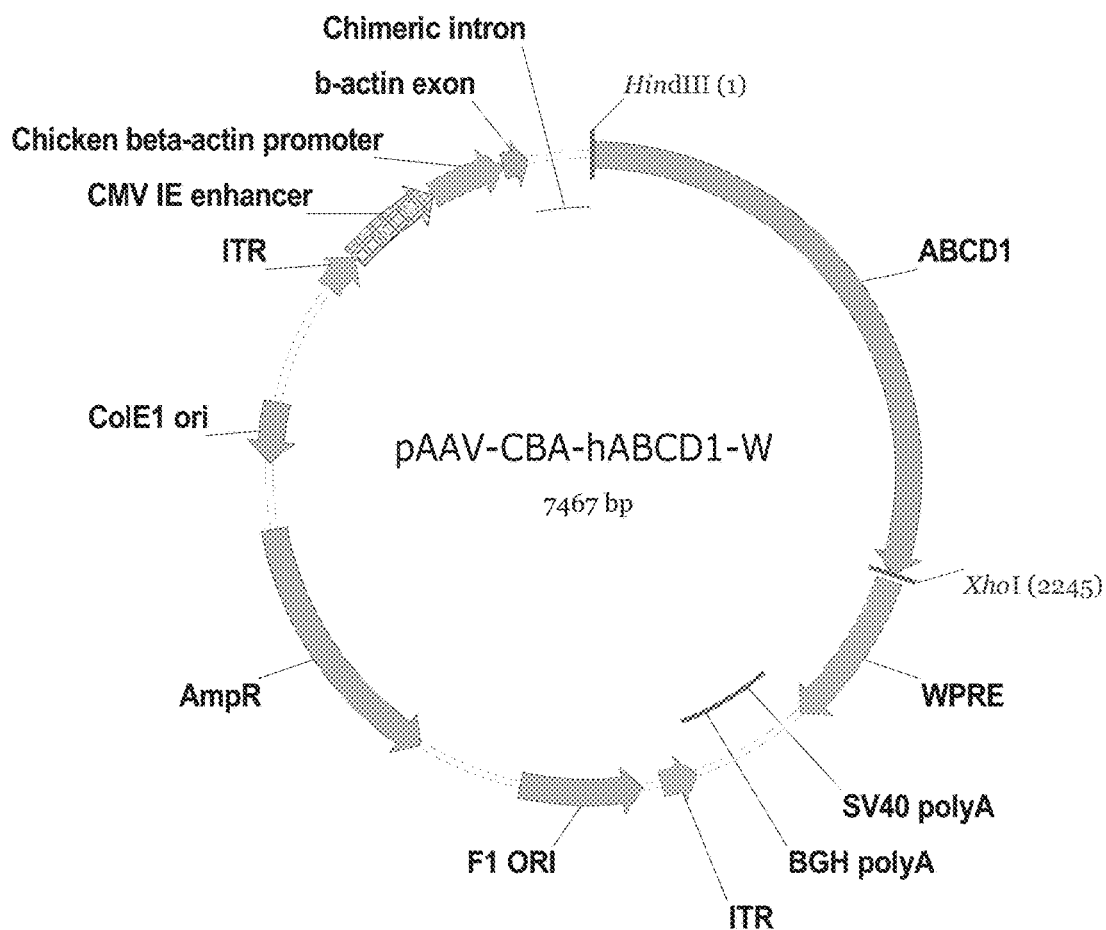
FIG. 8 depicts a vector map of AAV9-ABCD1.
Figure 9:
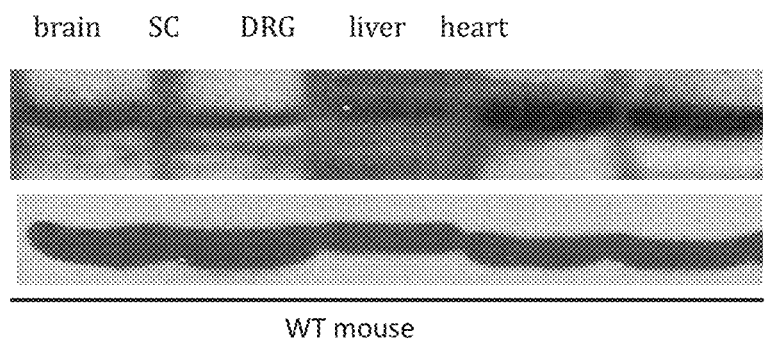
FIG. 9 depicts distribution of endogenous ABCD1 across different organs.
Figure 10:
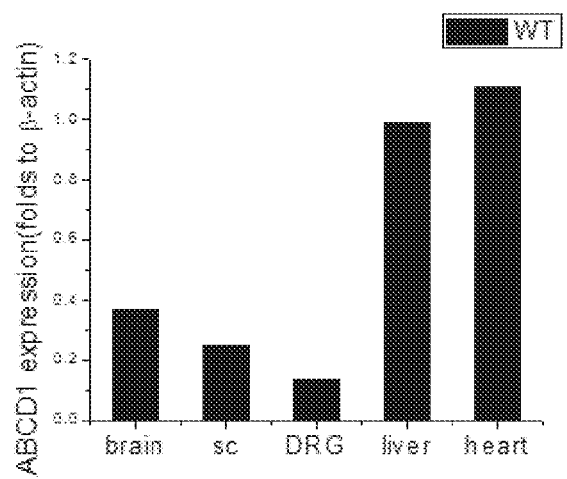
FIG. 10 depicts distribution of endogenous ABCD1 across different organs.
Figure 11:
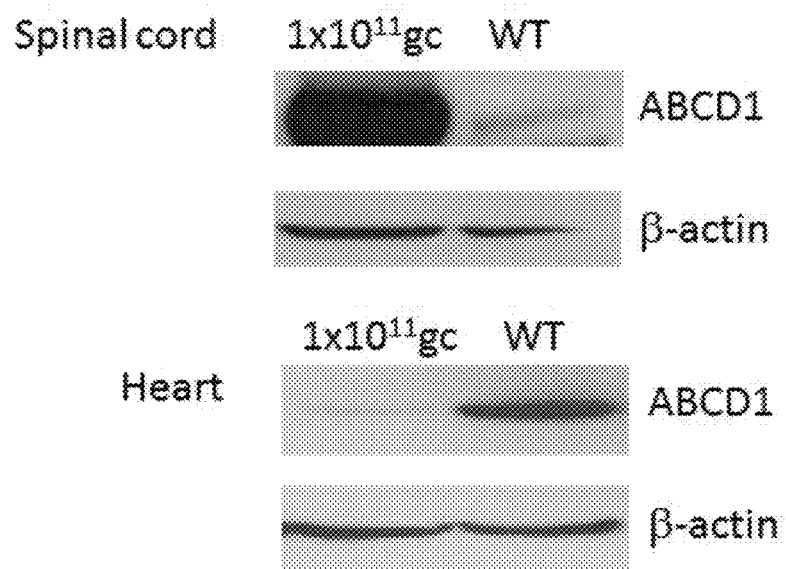
FIG. 11 depicts expression of ABCD1 after IT pump in Abcd1−/− mouse.
Figure 12:
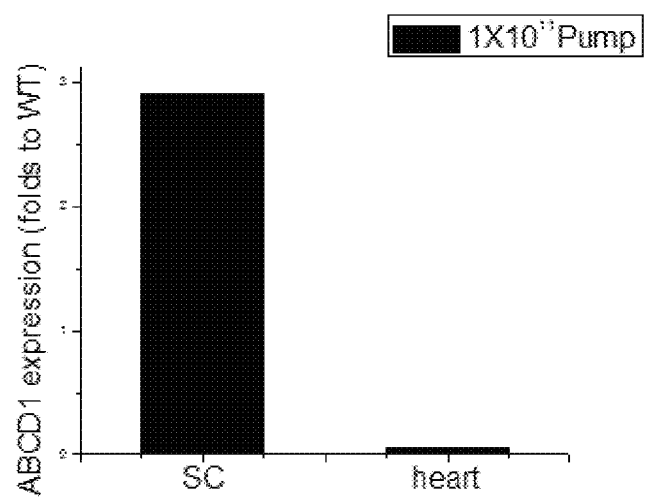
FIG. 12 depicts expression of ABCD1 after IT pump in Abcd1−/− mouse.

Notably, widespread expression of ABCD1 across CNS was even detected after low dose, direct intrathecal bolus injection of $0.5\times10^{11}$ GC (FIG. 5). For example, $0.5\times10^{11}$ GC bolus and pump delivery show similar expression of ABCD1 in the cervical cord, while heart tissue demonstrated higher expression after bolus injection (FIG. 6). It was concluded that the same dose delivered by pump led to higher expression in brain and spinal cord far from the injection site and comparatively less leakage to peripheral organs compared with bolus injection (FIG. 7). Delivering rAAV9-ABCD1 at $0.5\times10^{11}$ GC by intracerebroventricular administration results in behavioral improvement in the Abcd1−/− mouse despite localized expression in brain. Therefore, even better performance at this dose using the outlined intrathecal pump delivery can be achieved. At a dose of $1\times10^{11}$ GC administered via intrathecal pump, ABCD1 expression in the central nervous system was about 3 fold higher than expression of ABCD1 in the central nervous system of an untreated subject that does not have X-ALD (e.g., wild-type). Importantly, ABCD1 expression in peripheral organs was about 90% less than expression of ABCD1 expression in peripheral organs of an untreated subject that does not have X-ALD (see FIG. 11, where protein expression among different tissue types in Western blots was normalized to endogenous wild-type levels).

In conclusion, rAAV9-mediated ABCD1 gene transfer via intrathecal osmotic pump leads to more uniform and widespread gene delivery to the CNS with reduced leakage into the systemic circulation compared with intrathecal bolus injection.

Figure 13:
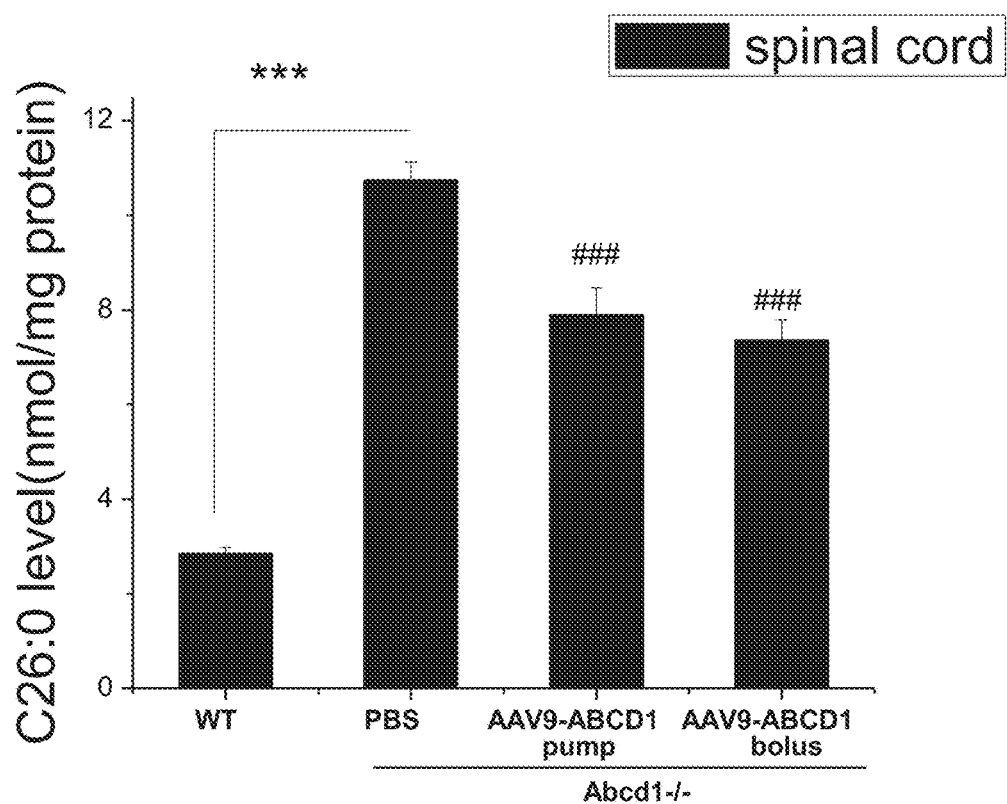
FIG. 13 depicts spinal cord C26:0 level 15 days after IT pump and PT bolus injection.

Example 3: rAAV9-Mediated ABCD1 Gene Transfer Via Intrathecal Osmotic Pump Leads to a Reduction in C26:0 Levels in the Spinal Cord C26:0 is the biochemical hallmark of adrenomyeloneuropathy. To assess for the presence of free very long chain fatty acids (VLCFA) after AAV9 gene delivery, lipidomic analysis was performed on spinal cord samples. Absolute values of C26:0 and C24:0 as well as ratios of C26:0/C22:0 are reported. It was determined that rAAV9-mediated ABCD1 gene transfer via intrathecal osmotic pump ($1\times10^{11}$ gc) leads to a 20% reduction in C26:0 levels in the spinal cord (FIG. 13). The levels after intrathecal osmotic pump delivery are comparable to those after intrathecal bolus delivery but avoid systemic leakage.

Figure 14:
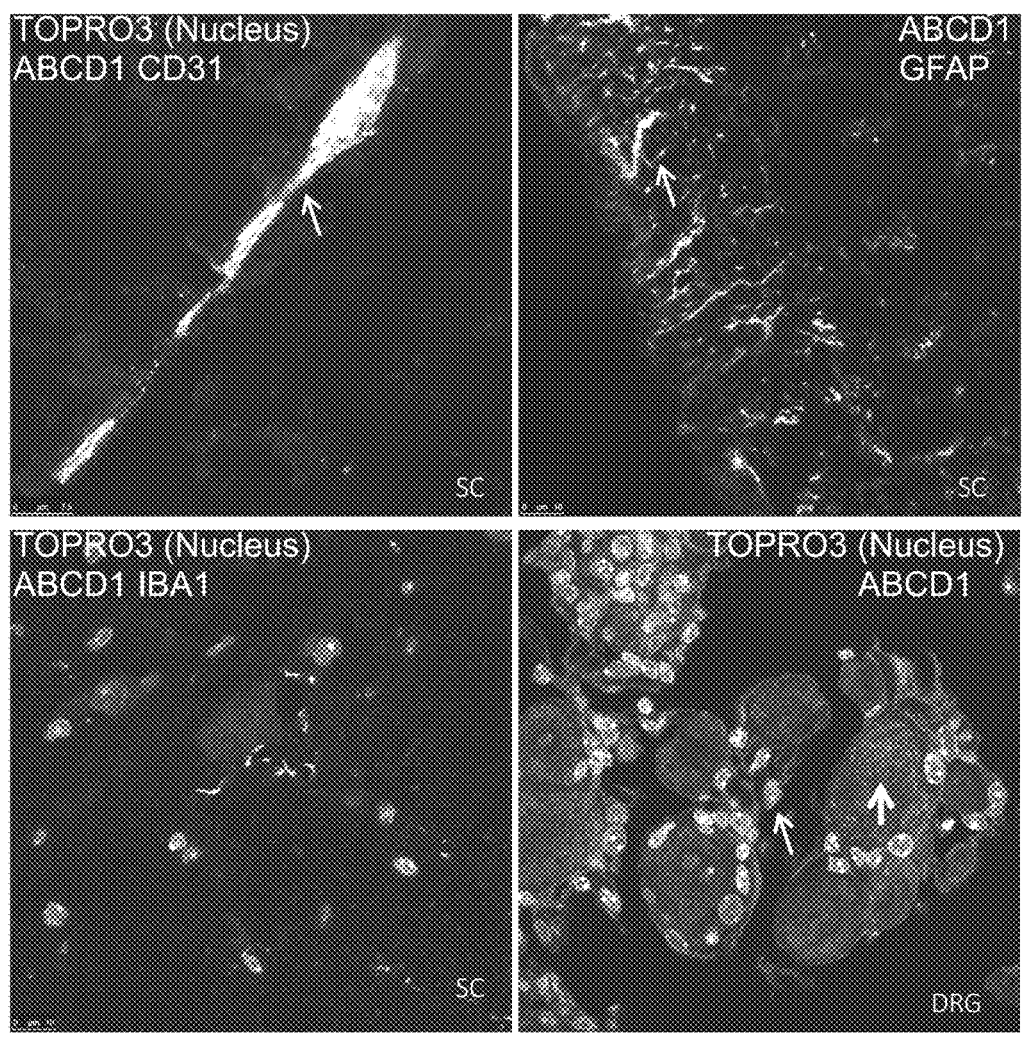
FIG. 14 depicts ABCD1 expression in different cell types after IT pump delivery of AAV9-hABCD1. SC: spinal cord; DRG: dorsal root ganglion; CD31: endothelial marker; GFAP: astrocyte marker; IBA1: microglial marker; TOPRO3: nuclear counterstain; DRG shows expression speckled pattern in neuron and more prominently around neurons (satellite cells).

Immunofluorescence staining and confocal microscopy imaging were additionally conducted. For tissue section imaging, sections of spinal cord (16 µm) were cut at −25° C. using cryostat (Leica) and stored at −80° C. Sections were stained with mouse antihuman ABCD1 antibody and then costained with rabbit anti-GFAP (Dako, Carpinteria, Calif.), rabbit anti-IBA1 (Wako, Richmond, Va.) and rabbit anti-CD31 (Abcam) respectively to localize the cell type. TOPRO-3 (Thermo Fisher Scientific) was used as fluorescent dye for nuclear counterstaining. The slides were imaged by confocal laser microscope and transduced cells counted. Estimates of ABCD1 transduced cells of each cell type were documented in 20× and 40× (for microglia) magnification images. rAAV9-mediated ABCD1 gene transfer via intrathecal osmotic pump ($1\times10^{11}$ gc) targets mainly astrocytes, endothelial cells and a few neurons in the spinal cord (FIG. 14). Within with dorsal root ganglia it targets both satellite cells and neurons (FIG. 14).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A nucleic acid expression cassette, comprising in order, an inverted terminal repeat (ITR), a cytomegalovirus immediate early (CMV IE) enhancer, a chicken beta-actin promoter, a beta-actin exon, a chimeric intron, a nucleic acid sequence encoding a functional ABCD1 protein, wherein the nucleic acid sequence encoding a functional ABCD1 protein comprises SEQ ID NO: 8, a woodchuck hepatitis virus posttranscriptional regulatory element (WPRE), an SV40 poly-A sequence, a bovine growth hormone (BGH) poly-A sequence, and an ITR.

2. The expression cassette of claim 1, wherein the functional ABCD1 protein comprises SEQ ID NO: 10.

3. A vector comprising the nucleic acid expression cassette of claim 1.

4. The vector of claim 3, wherein the vector is selected from the group consisting of adeno-associated virus (AAV), lentivirus, retrovirus, adenovirus, pox virus and alphavirus.

5. The vector of claim 4, wherein the vector is an AAV vector.

6. The vector of claim 5, wherein the vector is an AAV serotype 9 (AAV9) vector.

7. A composition comprising the AAV vector of claim 6 in a pharmaceutically acceptable carrier.

8. An isolated cell comprising the AAV vector of claim 6.

9. An AAV vector comprising an AAV serotype 9 capsid which has packaged therein a nucleic acid expression cassette comprising in order, an inverted terminal repeat (ITR), a cytomegalovirus immediate early (CMV IE) enhancer, a chicken beta-actin promoter, a beta-actin exon, a chimeric intron, a nucleic acid sequence comprising SEQ ID NO: 8 encoding a functional ABCD1 protein, a woodchuck hepatitis virus posttranscriptional regulatory element (WPRE), an SV40 poly-A sequence, a bovine growth hormone (BGH) poly-A sequence, and an ITR.

10. The AAV vector of claim 9, in a pharmaceutically acceptable carrier.

* * * * *

UNITED STATES PATENT AND TRADEMARK OFFICE
CERTIFICATE OF CORRECTION

| | |
|---|---|
| PATENT NO. | : 10,519,445 B2 |
| APPLICATION NO. | : 16/373081 |
| DATED | : December 31, 2019 |
| INVENTOR(S) | : Maguire et al. |

It is certified that error appears in the above-identified patent and that said Letters Patent is hereby corrected as shown below:

On the Title Page

Item (72), Inventors, Line 3, after "(US)", insert -- Yi Gong, Malden, MA (US) --

Signed and Sealed this
First Day of August, 2023

Katherine Kelly Vidal
*Director of the United States Patent and Trademark Office*

SEQUENCE LISTING

<160> NUMBER OF SEQ ID NOS: 10

<210> SEQ ID NO 1
<211> LENGTH: 19
<212> TYPE: DNA
<213> ORGANISM: Artificial Sequence
<220> FEATURE:
<223> OTHER INFORMATION: synthetically generated primer

<400> SEQUENCE: 1
cctcgactgt gccttctag                                                19

<210> SEQ ID NO 2
<211> LENGTH: 19
<212> TYPE: DNA
<213> ORGANISM: Artificial Sequence
<220> FEATURE:
<223> OTHER INFORMATION: synthetically generated primer

<400> SEQUENCE: 2
tgcgatgcaa tttcctcat                                                19

<210> SEQ ID NO 3
<211> LENGTH: 22
<212> TYPE: DNA
<213> ORGANISM: Artificial Sequence
<220> FEATURE:
<223> OTHER INFORMATION: synthetically generated primer

<400> SEQUENCE: 3
tgccagccat ctgttgtttg cc                                            22

<210> SEQ ID NO 4
<211> LENGTH: 19
<212> TYPE: RNA
<213> ORGANISM: Artificial Sequence
<220> FEATURE:
<223> OTHER INFORMATION: siRNA targeting ABCD1

<400> SEQUENCE: 4
cggaucaugu cgucguaca                                                19

<210> SEQ ID NO 5
<211> LENGTH: 19
<212> TYPE: RNA
<213> ORGANISM: Artificial Sequence
<220> FEATURE:
<223> OTHER INFORMATION: siRNA targeting ABCD1

<400> SEQUENCE: 5
cggaggagau cgccuucua                                                19

<210> SEQ ID NO 6
<211> LENGTH: 19
<212> TYPE: RNA
<213> ORGANISM: Artificial Sequence
<220> FEATURE:
<223> OTHER INFORMATION: siRNA targeting ABCD1

<400> SEQUENCE: 6
guucagcgcu gucacuuca                                                19

<210> SEQ ID NO 7
<211> LENGTH: 19
<212> TYPE: RNA
<213> ORGANISM: Artificial Sequence

```
<220> FEATURE:
<223> OTHER INFORMATION: siRNA targeting ABCD1

<400> SEQUENCE: 7
gaacgccugu gguauguua                                                    19

<210> SEQ ID NO 8
<211> LENGTH: 26895
<212> TYPE: DNA
<213> ORGANISM: Homo sapiens
<220> FEATURE:
<221> NAME/KEY: misc_feature
<223> OTHER INFORMATION: Genbank Accession No. NG_009022.2

<400> SEQUENCE: 8
ccacctggcc tggccttatc ccagagcctg ctttgccctt g gaccagttta tctttcaagc      60
acctgctagt gtacacctca atgtcagagt ttacagaact acagagctgg aacgacctgg      120
gaaaacctca gtctagccc agatgcagag aggtctagga tctctcccca agatatgctg       180
ccacacatct ctgtgttctc ctcctactac tacagggaat ggcaggactt cactgtgtgc      240
ttggttgctc agtcccccat tagaggccct gctccaggca attctgctgt ttaagtgact      300
ggtgagcagc actactcaga ccaaggtcac aggccagtta gcttctcttg gcttcagttc      360
tagagtgacc tgaggagcag cctcagaaac cttaggcgtc cctccttcca aggtcttgaa      420
aaaaagcaat gtaaggtggc cgtcataagc tgcatacaaa ctgcttggta taagcccacg      480
cccactgcta gaggggcctc tttttttttt ttttgagatg gagtctccct cttgttgccc      540
aggctggagt gcaatggtgc gatttaggct cactgcaacc tctgcctcgt gggttcaagc      600
aattctcctg cctcagtctc ccaagtagct gggattacag gtgcccgcca ccacgcccag      660
ctaattttgt attttcgta gagatgggt ttcaccacgt tggccaggct gatctcgaac        720
tcctcatctc aggtgatcca ccgacctcag cctcccaaag tgctgggatt acaggcatga      780
gccaccatgt acggcctaga ggggcctcaa agtgaagaac cgactagcgg tcagcagcat      840
gggcaaaggg agcctcttcc ctccctcaag agaaagacac agcatttcat tggtctgtct      900
cctagcagcc aaaactggat gctacacatc aaaagtggca aagggttttg cagcagagac      960
cagggtctag gtcaggtagc tgccctcagc catagctcac tcaccgatga ccaacagcac     1020
aaggatgaca atgagaacca caaagaaggt gttgccatag acactaaca actccaccag     1080 ccgggacttg aaaatcttct gccatctgtg aagaagacaa aaaggacagg agttgaagag     1140
aaagcacaca cacgagctct agggcccctga gcaaaatgga aatccagctt tgtactcttc    1200
tccaatggcc gaatagccca tgcaaagtca gcctcagtgg cttgcaattc tctaatttga     1260
catccattca agactattgg aaaaaaggcc aggtgcaatg gctcacacct gtaatctcag     1320
cactttggga gaccaaggtg ggtggatcac ttgaggtcag gagtgcaaga ccaaactggc     1380
caacatggcg aaaccctgtc tctactaaaa gtacgaaaat tagccaggcg tggtggtggg     1440
cacctgtaat cccagctact caggagggtg aggcaggaga atcacttgaa cctgggaggc     1500
ggaagttgca gtgagccgag atcgcgccac tgcactccag cctgggtgac agagcgagac     1560
cttgtctcaa aaaaaaaaaa aaaaaagat gctggtccac gtatagatca aaatgtctgg     1620
aaaactaatc tttttttttt ttttttgaga cagagtcttg ctctgttgcc caggctggag     1680
tgcagaggtg taagccaccg cgcccagcct ggaaaactaa tcttaaacgt gggcagttgg     1740
ctgggcgcac tggctcacgt ctgtaaaccc agcactttgg gaggctgaga tgggcagatc     1800
acctgaggtc agaagttcaa gaccggcctg gccaacatgg tgaactccca tctctactaa     1860
```

```
aaatatatat ataaaaaaaa attagctggg catgttggca ggcacctgta gtcccagcta    1920
ctcgtgaggc tgaggcagga gaattgcttg aacccgggag gtggaggctg ctgtcagccg    1980
agcaccacac cactgcactc cagcctgggt gacagagcaa gactctgtct caaaataaaa    2040
acaaaaacaa acaaaaaaac cacaacaaca aaaagaaaac atactggtag tctctgaaaa    2100
gggaaactta cttttcattg tactcccctt tgtaatattc aaatgtttgc cccatacacg    2160
ttatttcttt aaactgtctt tccacatgat aaaccttggt tgtctatat ccccgaccc     2220 tgttatgatg agatggaccc cagacctcac atcatttcca tccacaaatg ctttgggatg    2280
cagctctaag aagagacttc agaagtgttt acatattgtt caaatcaaca agaagccctc    2340
atcatcaggg ctagagttga atatgccaat cactgaaggc aatgatattt gtttgaatcc    2400
ggacccaaca aggtaccgat ttggcattcg gtagataaac gtcttaaatc cagcttattc    2460
tggaagctcc cccttccctc tccctctttc atttgctttt ccagtttcct ttgtgtagaa    2520
atcagattgt ctgtcctcta aagcttccca gattaaagct ccccggggcc ctctatctct    2580
gcacgtcttg tcaactgtac gaaggtgtgg ttttctacaa gaatcctcct cagacagcac    2640
tgcatacttt ctatggtatc acatcaaaga taattttttca cgaaaaaacg cttttaaaa    2700 atacctgtgg agatttggcc ttatttgtaa tatcgtaatt taaatagga tgtgttcagg    2760 tattatacat aattaaaatt aatctccaat tcacttttaa caggtcctct gttcattaaa    2820
agggaatatg gcttcatcct ccacaggctg agtaatgttc atgcagccac tgcgcaatac    2880
cagtgagact agttaggagg acaagagtca ccaaatcagc aacaacgtga cccagtggtg    2940
caagtcttcc gaatcccacg ctaccatccc agcaccccgt ggaccaagag tgggtgggag    3000
ggcatcattt ccagaactgt aacatagatc ttcctgcctc tcgggggcat tctgaagacc    3060
agaaggcagg ggacacagga aaaggaactg agcaagtcat gacgaagcag aaccctggga    3120
agggttggca ataacaaaca caacccctgc caccccacc ccagacaggt tctacctgtt    3180
ccatcgggtc ccaattccag ggtccaccag ctgcacacac cagtcccagg gctagggcac    3240
aggcaccctc ctgcctaact cgcctgcttg ctccataggc catacctttt aggagaaatg    3300
aagggaatgc agagaagcaa cacaacaaag acctccgcat agaggaaggt ggcaactgca    3360
gtccactgca gactcatcct gttgctagaa ggtttcccac aggaagatgt gagcttgttt    3420
cctggcaggg cacaaaaggt acgggacttg taagcgctgg gcagccaaga acatccagtt    3480
cagttaccct gcgaggctgg ggccgccact ctccaccctg acccctgca ctttgcttca    3540 aagtctctga tgcgctggcg gaagcagggc tccactcggc agggcctctt ggccagcagc    3600
gttcacaggc cccacaaact tccgttcgct ggtcaattac ctgccccctc cagcacgtgt    3660
gtcaacacgt ccagagcggc ctctcccgac gatccctgcc ccaggaagcc cgagatttcc    3720
gacgcccgtt taactgaaag gcgttcttcg ggaagagcag tgccagggca ccaagaggag    3780
gacgcctcgg cacccatcgg gcgctccctt ccccgcagg cagaactcag ccgcagaggc    3840
gggcgctctg cgggcccaaa tccccgctac caggcaggcc caaggccgca cctagtccaa    3900
gcgctgccga cgcccccgcc tcccaccgtc ccacggcgc ccgcggagag aaaccggcac    3960
ctccctcgag gatccagcgg ccttccgccc ggggccgctt cgcctccggt gggctggagg    4020
cccgcaagag cgactcctag agggcaggat tcgggaccaa gcgcaaaggc aggtctcgac    4080
caagcacctc aaggccccat acggagaaag ttctagacgc agtatcctca gaagccaggg    4140
gtccttacag tagccctcgc gggccccagc gcccacccag agcgaggggc ctccgacttg    4200
```

```
gccccggcct ggcacaccgt cccggaggcc catcccggcc gctcctccag gtggggcttc    4260
accgcccccc gccccgcccc cgagaccagc ttctagaggc gccgcccggt ttcccctcgc    4320
ccctgcctct cacacgcagg taggctgcgg gccccgagat tccccggccc cgggcctcc    4380 ccgcgccgct cgcctctctc cctcgtcgat gggccgggga gcctccgcgg tcccggagcc    4440
cagcccggcg cgcggagccc gctcaccgag tttcccacag tcaacgtgca ggccccgccg    4500
cagcaacaga actctcccac agcagccccg gccccgcccc tcataccgcg gccggaaacc    4560
ggaagcgccc gccgggcacc gcccaccagc cctcgcgagg ccccggaggc tccgcccacc    4620
tccgcttccc accccgcccc ggagcggagg gccggcgctc cgagcgggag aggaagaggc    4680
gcctcgggct ccgggcgagc agggcgggt ggagcgagca cgcgggcggg gcggggcggg    4740
gctttgtcgg gccggcgagg gccgcttctc tagtccgcgc ggccgtccca cgtctctgtg    4800
gtgcgggagg ggccccgccg aggggcgaga acggaggtg ggggtgtggg cgggccccgc    4860
cgaggggcga gaacaggggtg gggctcccgc gccggactc cgcccctcgc ccctcctccg    4920
cctcctcccc ttcccccgac tcgcccctgg ggaagagtgg gtgggattc tgggccggtg    4980 gaggagtcac tgtcgcttca gccaggctgc ggagcggacg gacgcgcctg gtgcccgggg    5040
gaggggcgcc accgggggag gaggaggagg agaaggtgga gaggaagaga cgcccctct    5100 gcccgagacc tctcaaggcc ctgacctcag gggccagggc actgacagga caggagagcc    5160
aagttcctcc acttgggctg cccgaagagg ccgcgaccct ggagggccct gagcccaccg    5220
caccaggggc cccagcacca ccccgggggc ctaaagcgac agtctcaggg gccatcgcaa    5280
ggtttccagt tgcctagaca acaggcccag ggtcagagca acaatccttc cagccacctg    5340
cctcaactgc tgcccaggc accagcccca gtccctacgc ggcagccagc ccaggtgaca    5400
tgccggtgct ctcaggccc cggccctggc ggggaacac gctgaagcgc acggccgtgc    5460
tcctggccct cgcggcctat ggagcccaca aagtctaccc cttggtgcgc cagtgcctgg    5520 cccccggccag gggtcttcag gcgcccgccg ggagcccac gcaggaggcc tccggggtcg    5580
cggcggccaa agctggcatg aaccgggtat tcctgcagcg gctcctgtgg ctcctgcggc    5640
tgctgttccc ccgggtcctg tgccgggaga cggggctgct ggccctgcac tcggccgcct    5700
tggtgagccg caccttcctg tcggtgtatg tggcccgcct ggacggaagg ctggcccgct    5760
gcatcgtccg caaggacccg cgggcttttg gctggcagct gctgcagtgg ctcctcatcg    5820
ccctccctgc taccttcgtc aacagtgcca tccgttacct ggagggccaa ctggccctgt    5880
cgttccgcag ccgtctggtg gcccacgcct accgcctcta cttctcccag cagacctact    5940
accgggtcag caacatggac gggcggcttc gcaaccctga ccagtctctg acggaggacg    6000
tggtggcctt tgcggcctct gtggcccacc tctactccaa cctgaccaag ccactcctgg    6060
acgtggctgt gacttcctac accctgcttc gggcggcccg ctcccgtgga gccggcacag    6120
cctggccctc ggccatcgcc ggcctcgtgg tgttcctcac ggccaacgtg ctgcgggcct    6180
tctcgcccaa gttcggggag ctggtggcag gaggcgcg gcggaagggg gagctgcgct    6240
acatgcactc gcgtgtggtg gccaactcgg aggagatcgc cttctatggg ggccatgagg    6300
tggggcaggt tggggtgccg ggcacggagg aagcgtgtg gcaggaggc ccgggggcag    6360 gcagccgtga gcggtgggga cagtctgggg cgggccgggg ctgatgccaa aggtgtgggc    6420
aggccatggg agagccgggc tgggggtgggc agggcctttg gcagccgtg gactcaggcg    6480 cggcagtgga gaggcaggaa ggctgggtgg ggactgtcct tgtgctggttg cctgcacgct    6540 cgaggccact tctgcttcct ctcctcctca aggaggttgt cctggcctta gagctgcgat    6600
```

```
cctagcggtt tgagcctcga gagctcctgc ccgccccact cctgcagcca gccaggagga   6660
gacgcctgcc attcatgagc ggggaccgag ggacgcagcc tgctgcctag cccctcctgg   6720
gcccttgggc cctttgaagg ccggcgtcca gcagagctgg ctggccaggc aggccggcat   6780
tatgggcatg actcagccca gcggaggtt aatgagcagc gcccagcaca gcagtgggac   6840
ttggggtcaa ggccaccccc gcctgagccc acaggcctgc ctggctacca actggctcag   6900
ctgccttccc gggcccccag accagagatg ccggggccag gccgccactg cggcgggaca   6960
cacttcctgc tcctggcgtg gctgtccttc aaccctgtc tgtctcctgg ctccctggtg   7020
ggccggggcc ggcgggccag acaggcgctg ggaaaggtta ctccaggtca atgctccctt   7080
tatctcgcct cagcccctcc ccttcctcgt gcctggggtt gcagctgcct tgggccctgc   7140
tctctgcgac tcagtttcgg ttccccagtg cttcttggga ggaggggcac aatggcatcc   7200
atcccccgaa ggctgtgtg tgctccctgg gtcaggtggc ctcttgccct gggaccttgt   7260
ctcactggct gtgcaccagc agagaagcag gcttgtcccc gaattccacg gagaggggca   7320
tcccgggtgt gggccagact gcagattcag agaaaaggcc cctggacttc agccaccacc   7380
ctggcttccc tctcctcttc tcccgcatgc tgggctgcag ggccttggca agcagctgca   7440
gccttgggcg aggcgcttgg cacattcccc gcagctacat tgtcagcctt ggctggcacc   7500
cctgccagct cccagcacga gtctggattg ccagggtgct tgcttcagga atggagatc   7560
gggcttgcag ggagctcagc tgtgcaggcc gacctgggtg gcggggcag aagagagatc   7620
actggttctt tgaaggcctt cgtccgggct agcttcagga agtagagaga ttactggttc   7680
tttgaagggc tagcttcagg aagtagcacg ttggccaaga gggtttgttg gccagggcag   7740
gagggcccgg tgtgcattca cggcctgtct gcataggcct cggctggaaa gctgtgtggg   7800
gtgagaggac cctcgggtag catgtggccc atggcagtcc cactggctga tgtccccgtg   7860
gacactggcc taggctcaga tcagggcaga agcagctgac tggctggagg gcacatagca   7920
gagtattctg tccttctgg gattgccgcg aggaggctta ttgaaacgca catgcacacg   7980
atctcttgtt tgagaacaaa gtaaagctct cttgataagt ctaagcatca tttacaagaa   8040
tgtggttctt ctggcagctc tgccagtgtg gtccaaattc ccacactggt tgccaccatc   8100
aggctgtatg ggcttgggca ggtcacttg cctccctggg cttcagtgtt ctgtgtacag   8160
tgggcacgtg aatacacatg cagtgggatg tggggagaat caaatgcaga gacgtgaaag   8220
cacttggcaa acagtggcag gctaggcagc tgtcatcaga cggctgtggg gaggcaaggc   8280
tggggtgcgt gcccctggac tgagcccaga aattcacaac cccttggcta ccttgctggg   8340
agcacttccc aacacctccc atctcccccg cctgtctgac tgctgctgcc acctcttccc   8400
tgcggctgtc cctttcccca cctgctgtg tcctgacata gtggtggcca gtgcaggaag   8460
ggggacagaa ggacagggga ggcctaccca ctgctgaggg agcaaggtcc aggctcagca   8520
gtggggacat ccactgggc gagtcctgta gggcccagct caggagcgca tcctcctggt   8580
ttcagtggga aaatgccatg caaatttctc accaaaagga agtgtgggaa agttgagggg   8640
aaagagggcg taaataggcc cagactgttg aaccgagttt ttcagaacca agagacaggg   8700
tttcactgtg ctgcccaggc tggggtgcag tggcgccatc actgcagctt caaactccag   8760
ggctcccgcg atcctcccac ctcagcctcc cgagtagctg gactacagg tgtgtgccac   8820
cacacctggc taattttttt ttttaattat ttttggtaga cacagcatct cgccgtgttg   8880
gccaggctgg tctccaactc ctgggctcag gcaatcctcc cacctcagcc tctcaaagtg   8940
```

```
ctgggattgc aggtgtgagc tactgcactc agcccaagag cactgccttt tgctgtcctg    9000
cgctgctctt tgcttagttt aggggggaa attagagctg atggatgatc tctccgagcc     9060
aggaggaggg ggctggcagg gagcccaaag aaatgggctc agcagaggac agaaacaagg    9120
tgactagaga gggagtggag aggggacggg agccgcactg tgacatcagc cagtcccta    9180 taccccctta caccttgagt ttgagacctg gccccaccca atcgtaacct ctggctctcg    9240
gccttctgat ggccaccatg gcacagcgtg tgtgagtggc actgggagac cctgaccatc    9300
gcccccacgg gagctgcccc tgtgcatggc caggaagcct ctctgtgtct gtcaccccc     9360 gcaggtggag ctggccctgc tacagcgctc ctaccaggac ctggcctcgc agatcaacct    9420
catccttctg gaacgcctgt ggtatgttat gctggagcag ttcctcatga agtatgtgtg    9480
gagcgcctcg ggcctgctca tggtggctgt ccccatcatc actgccactg gctactcaga    9540
gtcaggtgag acccagggct ccaagaggat ccaggccagg ggcctgtccc ccataccgct    9600
gggtgctgag ctcacgaggg cccaactcag ccagcccgcc gcccacttct gctgccgggg    9660
ccaccgaggc cctgctgcca gccttgatgc tttcagaggt tgagctcgcc ttgcccctcc    9720
ttgttgcctt tgccctgcg cgcacctcac gccctttgtt accactcaga caagcccagg     9780
actgcaagtc aggaacacta catgtcactt ctccaggcac agatacccctc acccacctgt    9840 ccctgtcctc aacccaactg cgacttagag gtgggagaat gtgcggagta cctggagtga    9900
gccccttcat cactccagcc ttggtttcct cgccctgaaa cagctcttgc accctaaggt    9960
gttttagagg agtgggaagc ctgttctacc tgttatttta gtgataagat taaatgttta    10020
ggtttctgca ttcctgttgt ttttgtttgt ttgtttatt ttcttttggg cttttgaaac     10080
aggagtctga ctgtcgccca ggctggagtg cagtggcgcg accttggctc actgcagcct    10140
caacttccca ggctcaagtg gtcctcccac ttcagtctcc ccagtcgctg ggactacagg    10200
cacaagccgc cgtacctggc taatttaat attttggta gagacagggt ttcgccatgt      10260
tgcccagact ggtctcgaac tcctggtcag gtgatcctcc cgcctcagcc tcccaaagtg    10320
ctgggattac aggtgtgagc tgccgcgccc ggcctgcatt cctgttttgt tcctctgccg    10380
gattgcaact tctgcatttg attttagtc cattagtggt cacccttaaa aaggtcaaca     10440
cgcagccggg cgcggggct cccgcctggc atcccagcac tttgggaggg tgaggcgggc     10500
agatcacgag gtcaggaggt cgagaccatc ctggctaaca gggtgaaacc ccatctctac    10560
taaaaataca aaatttagc cgggcgcggt ggcgggcgcc tatagtccca gctactcggg    10620
acgctgaggc agaagaatgg cgtgaacccg ggaggcggag ctggcagtga gcccagatag    10680
cgccactgca ctccagcctg ggcgaaagaa cgagacttcg tctcaaataa aataaaaat    10740 aaaaaataaa agatcaacac gcatacttgt taggttaatc aatagctccg ccttctcctg    10800
gaccttagaa cgcagaagca gccccgtggg gcatggcatc atagcccagc caagagttgg    10860
atttgtacct agttttttcct ctttgctatc gccttatcca cacgtgttga aactcactcg    10920
catgtttgct gagttctgtg ctcaccattt cgttcctaca tctcaatttc tcttctatgt    10980
tctgttatct tcctccagat agacatgttt ttagtttttt gtttgtttgt tttttaactc    11040
acaactatgc tcaggacaaa cagtcatcag tgcttctagt tgtggttggt ttttaaaaaa    11100
ggttctttca gcaagggttt tgtcatggga aattcttgat tatttattg taattctttg    11160 tgttgtttag tttttttgttt gtttgtttgt ttttgtaga ggcaggttct cgctgtgttg    11220
cccaggctag tgtggaactc ctgggctcaa gcggtcctcc cgcattagcc tctcaaagtg    11280
ctgggattac agacgtgagc caccacaccc aggctgttgt cattcttgat tatttttgtt    11340
```

```
gaaaatgttt ctatttcacc cttattccca agctaaagtt gagttgcgca atggagtcta   11400
ggtggactgt tcttttctct cagccctttc acaatgtctc attgtctccc tgcttcttct   11460
gtagctgctg acaaatctgt agctgctaac aaattgtcct ccctgagtac cctgtgtttc   11520 ttttttctg gtactttga tcactttctt tcttttggc attctgcagt ttcactatga       11580
catgtttagg tgtcagtttt tgttgattct gcttgagact tgttatatgt cctttgaata   11640
tttgagtttt tcaatcattc tggaagattc tcagctatta gctttcaga tattgcctga    11700 ctctcattct tttttcctgt tcttctagaa ctggcagcca gtgctggact tctgactctc   11760
ttcgttgtgt ctttcggttt ctgttactg tttcccatct cacactgtct gtgctgaatt    11820
ctggggatgc cctgaggcct tcctgtttgc tcattttcca gttcaccagt tttctctttg   11880
gccatgtcta attggaattt tgttcacatt tcagtggctg ttttgtaagt tctatttcat   11940
tctatttcaa ataggaattt gaaaatggac atttccttt tcaagtagaa atgtcaggct    12000
gtttctgtgt cttatttgct catcttttg actgctcctt ttatactgtg tatcaggtta    12060
gtcatactta ccccaccgtc tctatctgat ggtttggtta gcttcagttc ttgggagtat   12120
cattcgcctg tcttctgtct gctggtcttc actcatggtg gatcatttcc ttgtgggttt   12180
tgcaacagaa cttctatggg gattggtgtg gcctcaatgg agggtgtaag tccaaatgtc   12240
cttctgtttt ggccaagcac tccagggtaa gcagttggag gccattagtt agtgcggagg   12300
ggatggttcc tgaattgaga ggtggtttca tttgaattca tttgaactcc aggcacattg   12360
ttacaaattt tcagaggagg cttttttgttc attgggcata gagcccaggc taagcaagga   12420
aagcttcctg gtctttgccc tgcctgcctc tggggctatc aaaggatcac ctggctgtct   12480
gcttctcttt gctcccagaa gtttcccttg ctttccgtca agcttggctc tgctcgaaat   12540
agtgtcgtag tttacccagt ttggtgggaa gagggttttc gatttataaa cagaagtctg   12600
attctctccc tgttcctgtt tccacctcgg ggcttccatg ccctcaactg tctgtgtcat   12660
cctctgggtg actcaccaag aggaaggatc taattcgggg actgcacatc aagggcagcc   12720
ttgatgctgg cgtaggtgcc cagcccagtc agcgcaccta gccccgggca ccagacagc    12780 ccgcgagaca gcacctgcag ccgcttcgct ccatggctgc cattggtcac atcgggctgc   12840
tccctgccct gaaggcttag gacttttctg agcctctgct gtgccaggct ttgtgggctc   12900
ctggccctgc tctggtggtc ctcagagcca gcagcctttg aaggctgtga agcattccct   12960 ttccctggc ttgataggct ctgtcctgtg gccgtctgtt tttttttgga gggggagctt     13020
ttgagatgga gtctcactct gtctcccagg ctggagtgca gtggcacgat cttggctcac   13080
tgcaacctcc atctcccggg ttcaagtgat tctcctgcct cagcctccca agtagctggg   13140
actacaggta cacgccacca tgcctggcta attttttgtgt ttttagtaga gatgggtttc   13200
cgccatgttg gtcaggctgg tcttgaactc ctgacctcaa gtgatccacc tgcctcggcc   13260
tcccaaagtg ctgggattat aggtgtgagc cactgtgcct ggtcctgtgg ccttcttatt   13320
tccccaaatg ccaggcctgc tctgtcttgg ggcctgtgcc aggagcactc tttcctctgc   13380
tgccccatgg cgcagccccc ctaggcaagg cccggcctgc ccaccgccac ctttcctgtc   13440
tccttccctg ccccactgct ctcccaagca ctcgacaccc cgtcagtggc gcttttctct   13500
ctccctgcca tggactgcaa gctccatggg gtcagggatt tttgtctgtt ttgtccctgc   13560
tgtgtcccct gcatcgggtg gctagtgagg gctccaggtg cttcaaggag gtggagcgca   13620
ctgggtggga aggcaggctc ttaccggttg gaagatttag ataagctttg ctgggctggt   13680
```

```
gtgcaaggca ggtgggctca ggagatgggc agggcctgtg gctcccactc cagccctgag   13740
gccttgctct gtccagctct ggggccctgg ccttattcac ccaaggctcc aagagaacct   13800
gcagaaggca gctggttcta cgccaggatg ccctgggcac aaagacttgc agacccttcc   13860
ctttgtccac agcgactgtc cagctctcag aacacctggg gaggagggct gtgtccttga   13920
gagcaccgtg ggaaggaagg tccaaggcct tcgacccttta ggattcacat ccccgccccg   13980
ccagcccaat ctagttccct ggtttccgg gccaggcccc tttccaccct gcatggccct    14040
gagcggatac tgcgttccgt gtcttccccc agccccagc caatgatccc tgaggcttcc    14100
ccctcaggat cacacccacc cctggataca gtcctcgggt ccttcacagg acattcccac   14160
cacttcagcc acacccagc accctcagag gcggccttcg cccttgctcc ccacctctgc    14220
tcctgtgggg aatctaagga tcaagaaact gagagtcaag gccattgatg agggtcaggg   14280
gtgctgccac ggggcctaga gtgtgacaga aaagcaaatt aagacaggag cagctcctgg   14340
gagaagcaga caccaaacaa tacggctgct ggcccagagg tcaaaaacca tggcctagag   14400
ggggcggtca ggaagtggga cattaggccg ggcgtggtgg cccatgcctg caatcccagc   14460
atctttggag gccaaggcaa gtggatcacc tgagttcagg agtttgagac cagcctggcc   14520
aacatggtga gacttcgtct ctactaaaaa tacaaaaaaa attcgctggg cttggtggcg   14580
ggtgcctgta atcccagcta ctcgggaggc tgaggcacaa gaatcccttg aacctgggga   14640
ggcagaggtt gcagtgagcc aagatcacac cactgcactc cagcctgggc aacagagcaa   14700
gactccatct caaaaaaaag aaaagaaaaa aaaagaaag ttggcgtttc aaagccaaac    14760
agctctgggc gttggatgac aaagttcaga tgtgccccag gagggcgac atcagtggtg    14820 caggacagag ggccggtgga aggagctggc tgtacgtaga aacaaaacca gatgcctact   14880
ggtgcattta aaaatcaacg ttattggagac gtaattaaca tactatacaa ttcttccttt   14940
tccatgtaca gtttaaattc attcacagag ttgtgcagcc atcatcacta actccagaat   15000
gttttatttt tattttatcc cccaaagaaa ccccagaccc atgaacagtc actcctcatt   15060
ccctctctcc agcccctggc acccactcat ctgcttcctg tctctgtgga tttgcctatc    15120
tggacatgtc ctagaaatgg aatcatgtgc tctgtggcat tttgtgacta gcttccttca   15180
ctgagcatca tggtttcaag attcgtccat gtcataagat gaatcagtcc ttcattcctt   15240
ttcatggctg aataatattc cattgtgtgc atagaccaca atttctttat ccattcatcc   15300
cttgatggac attttgggtt tcttcatgtt ttggctattg tgaataacac tgctgtgaac   15360
atccatggac aagtctctat gtgtgcagat attttcgttt ctcctgggtg tgtagctagg   15420
agtagaattg ccaggtcaca tggtaactgg acgtttcact ttttgaggag ctgcgagact   15480
gttctccaca gtggctgccc catttttacct tcccgccagc agtgttggag ggttccacct   15540
tttcatcgtg gctagcactg gttatcatct cctttgtatt ctagccacct agtgggtgtg   15600
aggcagtatc tcttggtggt tttgatttgc atttccctga tgactaatga cgctgagcct   15660
cttttgatgt gttgagtggc catttgtatg tcttcttttgg agaaatgtct gttcacgtcc   15720
ttcgcccatg tgtgatcggg ttatctctgt cgctgagttg taaaagctct ttgtatattc   15780
tggatactgc accctcatca gatgtgtggt tcaccagtcc agagtttct cccagtctgt   15840 aggttgtctt tttcactgtc tcgatattgt cctttggtgc acaaaagtgt tgagttgaat   15900
gaggttcagt tgatctgttt ttctcttgtt gctcatgctt ttggtgtcct agtgaaggaa    15960
ctattgccat atccaaggtc gtgaagtttt atcccatttt cttctgagag tttcatactt    16020
tgggccacac tacacatcag cctgtgatgt gctctgggtt ggtttgtctg tatggtgtga   16080
```

```
ggggtccctc tcctgcacat agagagaaag agagagagag ctggttgccc cggcaccatt    16140
tgcagaagag cctcgccttt ctctccagcg gctcattttt gactttccgc tgtctctgcc    16200
ctgcccctcc ccgccccgcc acccacccct ctggggcttt gcagatgcag aggccgtgaa    16260
gaaggcagcc ttggaaaaga aggaggagga gctggtgagc gagcgcacag aagccttcac    16320
tattgcccgc aacctcctga cagcggctgc agatgccatt gagcggatca tgtcgtcgta    16380
caaggaggta ccctggccc agccccaccc ttgccatcct tgccatgctt ctctccctgc    16440
aactggcagg ggctgagcca gggtcaccct ccctcaggtg acggagctgg ctggctacac    16500
agcccgggtg cacgagatgt tccaggtatt tgaagatgtt cagcgctgtc acttcaagag    16560
gcccagggag ctagaggacg ctcaggcggg gtctgggacc ataggccggt ctggtgtccg    16620
tgtggagggc cccctgaaga tccgaggtaa ggctgtcccc tccctatgag tgaccccgcc    16680
cctgctgctg ctgcaggtgc tgacctgctg ccccagctcc tcctattccc gctccctcac    16740
tcagggacct ccatgtgctt ctggcccatc ccagtccacc caggacggga gggctgccgg    16800
gcagggtctt tgaggacttc ggcctggtcg agctgggccc ctggagggtt tcctgcagag    16860
aggtgctggt ccgcccgcct tccttcccag acagtagctg ccggccaccg tactgactcg    16920 cccctttgagg gcctcagcct ggattattca ttcaaaacaa gggggatgtg gtcccctcac    16980
ccatgcagga cagcaagaga aagttccagt cagtgtgcca gctgctggct gccacggag    17040 gcaggtgctg cagaagggag tggcggccca gggcactgta ttagacactg ggggaagagt    17100
tcagcttgtt ggaagacctg gctgtgttcc ctagggaccc tggaccacag gctgctggtc    17160
aggaaccagc tggcatgctg ccagggatgg gaatgagggc gtgcagccag gggcacgcag    17220 actcccaga atgcagaggg gtcgccacca ctccctctcc accccagccc cgctgtgctg    17280
tctctgcagg ccaggtggtg gatgtggaac agggatcat ctgcgagaac atccccatcg    17340
tcacgccctc aggagaggtg gtggtggcca gcctcaacat cagggtaggt ccagcgggga    17400
gggcgccagc cacgcacata tgcaagcctc agcccttggc ttcccgcctg tctgtgctgg    17460
caacagccat tgtccctaga tgtacgtggc aggtgggcca aggtcaaggt gagagaccaa    17520
cgtgtctctg actgttcatc ctgggcaac agaggcaggg ctcataaaag agactagtga    17580
taccaggatt gaccaaggtt caccccggcg ttcctggccc tatcatctga tgccaactcc    17640
ccacactcct aagaaagcca agacccgggt ggggggggctc tggttcaaac cttgccgctc    17700
gacctccctc ggaaggccac agcaaggaat ccacagatca cctgtgtccc cagccagggg    17760
tttggacagg gctggggagt aatggagtga ggggagact ggggtggagg gacaggtaga    17820
gaagtgacaa ggaatcactc attcattcac tcatttaacc aatgtgccct gaactctgag    17880
ccgggcacca gaaacccgag gtaaatcagg agacctgcac tcagggagtc ttcactgtgg    17940
aggggcacta aagtgttaca aagggtctcc aggtagacag ctgttcaagg gacagtgggg    18000
gtcacaagaa gagtggtcag agtccctggg ggtggtgggg gtgggatgaa gccttgccca    18060
ggagttgctg tgagcgagtg ggcaggcagc tgagggtaga ggagtgaggg gccgtgggcc    18120
tgaggggcag gtcacgcagg aggaagcaga gaggaggggc atgccaggga ggaggggcc    18180 ggcacaggtg gttacccctc accgctcgca gcggcccctc ctaggatgtc ggggagctg    18240 atcaccagtg agtccaagga aggtggtttc caggctggcc ccgggcagca caagcaggca    18300
ggggcagcgc gcaagctcat ggggcccctg cgcgcagggc cacatatgct cagggagccg    18360
ggtatgcgag atggggcaag gcccaggccc caccttcag gaggggacag tcaggtggct    18420
```

```
tcattagcat cctgtggctg cggtcacaaa gcgttacaaa ctttgagtgg ctttcccagc    18480
agagatggcc tctctcccgg ctcggggaat agcagtccga gaggaaggcg caggcagggc    18540
gggcttctgc caaggaccga gaaggtgcct ccgctcgggg cctctgtccc agcttctgct    18600
ctgctgccca tctgcgggct tccctggctt ctgccacggc aggtcggcct cagcctctgt    18660
ctccacacgg cgctctccct ctgggtgtgt ccgtgtctcc gtctcccctt tctgtcagga    18720
cacaggtcac actgcattag ggcccacccc tctgcagaat gacctcatgc agacctaact    18780
catcacgtcc gcaatgaccc tgtttccaaa taagctcaca ctccgaggta gtggggatta    18840
gggttcccac ataggaattt cagaggacag agttccaccc atgacactgc ctgaggtaag    18900
ctaaagacca cggcctcaag tcttcccagg agcccgtgt agcattgttg ttgttaccgt     18960
gaacttcact gactccaggc ccctggcctc ctccctgcac acagcccgcc tccagcctgg    19020
ccggcatttt cccaaagtag gcatttccta gctccagcga ggaccatgga gtcagtgaat    19080
tgaggagcct gaggtccatg atgcagagcc caggggccac tgtggcatct ctgggccact    19140
ctggcacctg ggaggcagt ggggtctgta ctgtcagtct agagacataa agaaagtgct     19200
tttttgggccg ggcgtggtcg ctcatgcctg tcatcccagc actttgggag gccgaggtgg   19260
gcagatcgct taagcccagg agttcaagac cagcctgggc aacatggcaa accccgtctc    19320
tacagaaatt tttaaaaata cacaaataag ccaagtgtgg tggcggtgcc tgtagttcta    19380
gccacttgaa aaaaaaggct aaagtgagag ggtctcttga gcccaggagg ttgagcctgc    19440
agtgagccat gatcccacca ctgcactcca gcctgggcaa cagagcaagg ccccgtctca    19500
aaaagaaaag aaagaaactg ccttttgtcc ccagtgactc aggaggccaa ggtgagagag    19560
tcgcttgagg ccaagagttt gagaccagcc tgagtaacat agcaagaccc tgtctctaaa    19620
acaacattta aaaattagcc aggcatggtg gcgtgcatct gtaggccag ctactcagga     19680
ggctgaggtg ggaggatcac ttgagcccag gagttggaga ctgcggtgag ctgtgatcat    19740
accgctgcac tccagcctgg gcaacagagt gaggtctcgt ctcttgaaaa caaagtgcct    19800
ttcagggcag ttccttaaag ggggctgaca gttgaccctg cacttggatt cctggtgaag    19860
tgggagtcgg atgggactga ggacggcgct ggctgtgttg gaacacacct actcattcag    19920
ctgtggcaga ataggcccctt cctcttgtgc tggcaccatg ttctccaggc gtgtcagggc   19980
ctgaggactg ggccggggct tgtccattcc tgtgtcctgg gccaggcatt tagcgagagc    20040
caaatttagc tagggctgtg gacgctggac cccatccccc aggccctgct gtcccttatc    20100
aagagatcaa gaatgcctg cgtgctggcc tcgggcattg ggagcctctc aaggctggtc     20160
aggaggccat agggtacggg aaggggcctg cgctctctgg cgtcagcggc tgttgcccct    20220
gcaggtggag gaaggcatgc atctgctcat cacaggcccc aatggctgcg caagagctc     20280
cctgttccgg atcctgggtg ggctctggcc cacgtacggt ggtgtgctct acaagccccc    20340
accccagcgc atgttctaca tcccgcagag gtaaggaagc ccgtgcgcct ctcctccacc    20400
tcttcctgcc tgtgcgctca cacatggctt cctgcagagg cccaggaagt ggtgaagagt    20460
cagcacctca ggagaggaca ctgaggcact gtccccagag ccagagacgg gctgtggttc    20520
ctgctccctc caacccgcc cgatccactg ccctgttttg gatctgtgtg gggtgtgtgc     20580
acgggcggcg atgtgagcgt gtggatgcgt gtgagcgtgg catgtggaca ctgcctggga    20640
ggcgcagagt atcttggggg aggcagagcc ggcccttccc tccgtggaca cccagctttc    20700
ccacaggccc tacatgtctg tgggctccct gcgtgaccag gtgatctacc cggactcagt    20760
ggaggacatg caaaggaagg gctactcgga gcaggacctg gaagccatcc tggacgtcgt    20820
```

```
gcacctgcac cacatcctgc agcgggaggg aggtaggagg cctggggctg gcagccaccc    20880
tttgtcccac cctggcctct cccttggcct ccagggagtg aagattacct caacatccag    20940
agtctaaagt gccaggtgcc acggggcggg gcagaggctg ctaccaggga ggaccaacac    21000
cacacagatg gccccaggtg ctctaggaa gggggcacct agcagggatg tgcacctcac    21060
tgggggaccc aggatacct ctcccagaga aaagaggtct gagctgagcc ctgcagaatg    21120
ctgagtggtt accccgtccg gaagccaggg gcagcagggc ggagtgcgtt ccgaaggctt    21180
ggtggtgcga gaggctggct cacagagggc cctcgggacc aggcgggagc ctaggctttc    21240
cctgagcagg atcagacgct cttggaagga ccatggggtg gtgggcaggg gcagcctggg    21300
aggggcaggc acatgtgtgc agtgatggct actgtcaaga ggtttgtgca gacgcttgga    21360
gggggctggg gccagcagag tcaggtggat tcagagatga gttcactgaa aaggaggcca    21420
gactgagctg ttgtcttgtc ctgggcttat caaggaatac tgcttgtcca cagtgtctgt    21480
cgggccggaa gagcggagga ggagagggggg ctgcagctac agggacacag tagatggagt    21540
gttcagttct gtcttttgaat tctgagcctc tgggttctgc ttccagcctg cactgctggg    21600
tgcgagatgg ccctgggcaa ggacctcgcc ttgctgggc tccccttcac ggttcaaggg    21660
cacgggcacc aagccctccc tcggtggcaa catgagaaga agtggctcct gcaggaaatg    21720
gccggggtgt tgtcacctgc ctgtggagga agcggggaca caggtggcaa tggcagtgga    21780 gcagccctg gccggccct gcctcttgct cctgctgccc tcagcctggg agcacgtggc    21840
ccctcccgcc tctgtggcag cctgaatgcc cagggcctgt ggccggccag catgagccat    21900
taggatggag ttgagctgcg aggaacagaa cgggcctccc cgcaatagtg gctaagatca    21960
tctgtgagtt tatcctactg agctgttagg tcccaagaga gccaggccac ggttgccagg    22020
gctggccctg ctctgtgaag gccccagggc tcgaggattt tctaccaggt cactctgctg    22080
tgtttggcct ccgttcccaa agtcacctca tgatccagga gggctgctgc agccctcaca    22140
tcatgtccca ggctgtagga tggaggaagt agaagggaag gggcaaaagg tatgtgcctt    22200
cttttaagga aggttccaga agccgccata ttgaatactt acagttatat ctcattggcc    22260
acaacttagt ctcatgctca cacctcatca caaggccacc tgggaagcgt aatctctact    22320
ctgggtggcc atatgccctg ttgccacttc tagccctggg ccgctgggga aggcagcatg    22380
ggcgagaaga caggaagggc cgcttctgcc gcagcgcccc gacctaatgg agcagccggc    22440
tcacctgctc gttcaagcag cccactcgag ccttgccaaa gtgctgacac ggggcagtga    22500
caggaggccc aaccctgtg ggtgacaagc ccccggtctg gggagagcac tcaggccgct    22560
ctggagctct gtgccaagga actgtatggg tgccctgggg ctgccataaa ccgcagggat    22620
ggattgtctc ctagatccag cagtccgaga tccaggtgcc agcagggtgg gctccttccg    22680
ggtgccatga cagaaggatg tgttccaggc ctctgtcctc ggctcgcaga tggtccactt    22740
ctccctgtat atcttcacct catgttcccc tgtgcatgtc ttctgcccac acccccctt    22800 tttatgagga cacagtcata ttgaattagg gtccactctg atgacctcat cttagtgtga    22860
tcacctctgc gaaggccctg tctccaaata aggtcacact gaagtgttgg ggcttggact    22920
ccaccgtatc tcttctgggg gaaggcacga ttccagtccc cactcctcca tgattaatgc    22980
ctgtcagaca gacaaggacg cagaggcaca ggggccctgt cgtcacagct agctcattcc    23040
cgcagctccc ccagctcccc ggctggcccc cgggtctggg tgctggtgga actgagccaa    23100
gaccattgcc cccgcctagg ttgggaggct atgtgtgact ggaaggacgt cctgtcgggt    23160
```

```
ggcgagaagc agagaatcgg catggcccgc atgttctacc acaggtgagc actccgggcc   23220
ggcaggctcc ctgggtccc ctggaagggg aagtagcagc tgtggggagg cctgggctca    23280
gtggagcctg agccgggctg gggtgttggg ccctggaggg tgcacagact ctcctctcgg   23340
cccggacccc caggcccaag tacgccctcc tggatgaatg caccagcgcc gtgagcatcg   23400
acgtggaagg caagatcttc caggcggcca aggacgcggg cattgccctg ctctccatca   23460
cccaccggcc ctccctgtgg taggtgccct gtctccctgc ctggggtcgg tgggagtggc   23520
tgcctgaggg gaggaggtgg cctggcgggc ccggcagcag caggcggctg tcatcagcag   23580
cccccgtgcc gtgcccctga ccctgtccct ctcctggcca ggaaatacca cacacacttg   23640
ctacagttcg atggggaggg cggctggaag ttcgagaagc tggactcagc tgcccgcctg   23700
agcctgacgg aggagaagca gcggctggag cagcagctgg cggcattcc caagatgcag    23760 cggcgcctcc aggagctctg ccagatcctg ggcgaggccg tggccccagc gcatgtgccg   23820
gcacctagcc cgcaaggccc tggtggcctc cagggtgcct ccacctgaca caaccgtccc   23880
cggcccctgc cccgccccca agctcggatc acatgaagga gacagcagca cccacccatg   23940
cacgcacccc gccctgcat gcctggcccc tcctcctaga aaacccttcc cgccctcggg     24000
aaagtagatg tggagggtgg cgccctgcgt aaccctcgcc ctgtccctcc cactccctgg   24060
gggcgctgtt ccacagtgac tgggccctgt ccagggcagt gagtcctcta ctttgctccg   24120
tggaggaagc tgggtacaa ggggcccagt gctggccaca cagcagcgca gccgagcccc     24180
aggagcccgt caggccacag cccctggcac tgcaggtggc ctccctccag agactcgagt   24240
ccccatgatt ccctcctcgt cagtctctca aagaccccat ggtccatccc ctgagggtgg   24300
tcagccaagg ctcccgttcc gtgggatgcc ataaaagccg cccagtggga cccacagtca   24360
cacagagcgc ctcacctgca tcctctcccc cacaagagcc ccaaagatcc cacgggagag   24420
gggagaggga cgcacagcac tgcctgccaa gcgagaatgc aggccccgcc ccctcggccc   24480
ctcaccacct ctttctacag cctaatttat tggattccct attcgtagcc atctccgtgg    24540
ccaatgtgac taccgtgcca gcagcggggg cggcccagcc tctgagtccc gtggggcccc   24600
ggctcccacc ggtgccaaac ccagcccctg cggccgtcac cccgccagcc tacactgcca   24660
gccgccaccg gggcacacgg gcctctgctt gccagccagg agtgcggaca ccatgttccc   24720
agctcagtgc caaagagggg tcaccagggg gagctgtctg cggagccagc gcctgcccga   24780
gagagacccc accgccaccg tgtgcctttc ccgggccctc agccctcggg ccgggcacca   24840
cccccagtcc ccccagtaaa agcctccact ggcaaatgca gtccttcctc cctgcctcag   24900
agcctggtgg tgtctgctgt gggtctcgag gagagatgga ggagagggag tgggttgcct   24960 gtggggaaa gagtgagttt gggaaaggag tgggcctgac ccccaagccc ctccgagggg    25020
gaaagtcacc agaagacatg gtccagcatg ccctccgccg agcctcacgc caatgctctt   25080
aggattcctg tgacggtggc ggggcggaac ctgcaacaac attgcacaga aatactggct   25140
gagcccaaat aggactaggg gaggggatca tgctggtccc tgtgggagga gcacgaaggc   25200
aagagaaggg atgtctaagc tgccacacag ggtgctgctg gcccttctag ggagaggcgg   25260
ccacttgtgc aggggcctgg ggggaactgg gagcacagcg cagggtgttc gtgctgcatg   25320 cagggggaagg gagggcaggg gaagggaggg ctgcggccgg cgggccttgg aggccacact   25380
acagagacag gacttagccc agaggccacc gaggagcttt cagcaacagg gaagcagtgt   25440
cgagtactgc aggccacgtg gctgcatgtg agggtggctg gtgggaatag ggtgcggcag   25500
cccatctggc ctcagaggca cgagaactga gaacagctgt gcggccatac ctttatgcat   25560
```

```
ggatggccac agcctcccaa aggtggggca gcctgagtgt tcatcaacag acaaatggac    25620
aaacagcctg tccataaggc acagtgccat tctgccataa cacgcagat agacctcaaa     25680 gagttcgtgc tgggtgaaag aagccagaca caaatgtcca gataggctc atcgggacag     25740 aaagcagaca agtgggtgtc aggggctggg gcaggggaag gaaaatgtgg cggggggagt    25800 ccttttaaa aaattttgta tttattttt atttttaat gagacagaca gggtctcacc       25860
ctgtcaccca ggctggagtg cagtggcgca gtcataactc actgcagcct tgatctcccg    25920
ggctcaagca atcccgcccc agcctcctga gtagctggaa ccacaggcgt gtgccaccat    25980
accctgctaa ttttgtgatt tttttttttt ggagacagga tctcactatg ttgcccaggc    26040
tggtctcaaa ctgctgaact caagcgatcg tcctgcctca gcctcccaca gtgctggatt    26100
acaggcatga gccaccacac ccagcctcgg gtttcttttt atttcgaaga aaatgttctc    26160
gaactataga gcatactaaa tgccactgaa ttatgcactt taagggatt gattgtatat     26220 tttgtgaata tcgcctcaaa aacagatgat tgatggataa attgatacat agatatatag    26280
atatatagac atgattgata tagatgattg attgatagat gatggatgat tcataggtga    26340
taagtgatag ataaaataca tgatagatac atggatagac agatgaatag agagagatga    26400
tagatggttt taaaagtttt tttagagaca agatctcact atcttgccca gtctggactc    26460
gatctgctag catcaagcag ccctcctacc tcagcctcct gagttactgg gactacaggc    26520
acatgctact gtgcctggtg atagataaat gattgaaaga tagacatgat agaggcataa    26580
atgatagata gatggataga catgataaaa ggaagataca tgggatagat caatgattga    26640
ttatataagt aaatgatata aattgataga ttattgatta tagattaata ggcggatagt    26700
tgattgatag atgattgatc gattgattga ttgattgatg agagagaca gagaagcaag     26760 cacagccatt gcagccaccc agacaagaca tgctgaggcc tgaagttcca gaaggttcga    26820
gcagttggaa gaactcaaca ggcatggggg cagcttcttc agggagtgga gggggcagca    26880
aggtaccact gggtt                                                     26895
```

<210> SEQ ID NO 9
<211> LENGTH: 3697
<212> TYPE: DNA
<213> ORGANISM: Homo sapiens
<220> FEATURE:
<221> NAME/KEY: misc_feature
<223> OTHER INFORMATION: Genbank Accession No. NM_000033.3

<400> SEQUENCE: 9

```
gccaggctgc ggagcggacg gacgcgcctg gtgccccggg gaggggcgcc accgggggag     60
gaggaggagg agaaggtgga gaggaagaga cgcccctct gcccgagacc tctcaaggcc     120
ctgacctcag gggccagggc actgacagga caggagagcc aagttcctcc acttgggctg    180
cccgaagagg ccgcgaccct ggagggcct gagcccaccg caccagggc cccagcacca     240 ccccgggggc ctaaagcgac agtctcaggg gccatcgcaa ggtttccagt tgcctagaca    300
acaggcccag ggtcagagca acaatccttc cagccacctg cctcaactgc tgccccaggc    360
accagcccca gtccctacgc ggcagccagc ccaggtgaca tgccggtgct ctccaggccc    420
cggccctggc gggggaacac gctgaagcgc acggccgtgc tcctggccct cgcggcctat    480
ggagcccaca agtctaccc cttggtgcgc cagtgcctgg ccccggccag gggtcttcag    540
gcgcccgccg gggagcccac gcaggaggcc tccggggtcg cggcggccaa agctggcatg    600
aaccgggtat tcctgcagcg gctcctgtgg ctcctgcggc tgctgttccc ccgggtcctg    660
```

```
tgccgggaga cggggctgct ggccctgcac tcggccgcct tggtgagccg caccttcctg    720
tcggtgtatg tggcccgcct ggacggaagg ctggcccgct gcatcgtccg caaggacccg    780
cgggcttttg gctggcagct gctgcagtgg ctcctcatcg ccctccctgc taccttcgtc    840
aacagtgcca tccgttacct ggagggccaa ctggccctgt cgttccgcag ccgtctggtg    900
gcccacgcct accgcctcta cttctcccag cagacctact accgggtcag caacatggac    960
gggcggcttc gcaaccctga ccagtctctg acgaggacg tggtggcctt tgcggcctct    1020
gtggcccacc tctactccaa cctgaccaag ccactcctgg acgtggctgt gacttcctac    1080
accctgcttc gggcggcccg ctcccgtgga gccggcacag cctggccctc ggccatcgcc    1140
ggcctcgtgg tgttcctcac ggccaacgtg ctgcgggcct ctcgcccaa gttcggggag     1200
ctggtggcag aggaggcgcg gcggaagggg gagctgcgct acatgcactc gcgtgtggtg    1260
gccaactcgg aggagatcgc cttctatggg ggccatgagg tggagctggc cctgctacag    1320
cgctcctacc aggacctggc ctcgcagatc aacctcatcc ttctggaacg cctgtggtat    1380
gttatgctgg agcagttcct catgaagtat gtgtggagcg cctcgggcct gctcatggtg    1440
gctgtcccca tcatcactgc cactggctac tcagagtcag atgcagaggc cgtgaagaag    1500
gcagccttgg aaaagaagga ggaggagctg gtgagcgagc gcacagaagc cttcactatt    1560
gcccgcaacc tcctgacagc ggctgcagat gccattgagc ggatcatgtc gtcgtacaag    1620
gaggtgacgg agctggctgg ctacacagcc cgggtgcacg agatgttcca ggtatttgaa    1680
gatgttcagc gctgtcactt caagaggccc agggagctag aggacgctca ggcgggtct    1740
gggaccatag gccggtctgg tgtccgtgtg gagggccccc tgaagatccg aggccaggtg    1800
gtggatgtgg aacagggat catctgcgag aacatcccca tcgtcacgcc ctcaggagag    1860
gtggtggtgg ccagcctcaa catcagggtg gaggaaggca tgcatctgct catcacaggc    1920
cccaatggct gcggcaagag ctccctgttc cggatcctgg gtgggctctg gccacgtac    1980
ggtggtgtgc tctacaagcc cccacccag cgcatgttct acatcccgca gaggccctac    2040
atgtctgtgg gctccctgcg tgaccaggtg atctacccgg actcagtgga ggacatgcaa    2100
aggaagggct actcggagca ggacctggaa gccatcctgg acgtcgtgca cctgcaccac    2160
atcctgcagc gggagggagg ttgggaggct atgtgtgact ggaaggacgt cctgtcgggt    2220
ggcgagaagc agagaatcgg catggcccgc atgttctacc acaggccaa gtacgccctc    2280
ctggatgaat gcaccagcgc cgtgagcatc gacgtggaag gcaagatctt ccaggcggcc    2340
aaggacgcgg gcattgccct gctctccatc acccaccggc cctccctgtg aaataccac    2400
acacacttgc tacagttcga tggggagggc ggctggaagt tcgagaagct ggactcagct    2460
gcccgcctga gctgacgga ggagaagcag cggctggagc agcagctggc gggcattccc    2520
aagatgcagc ggcgcctcca ggagctctgc cagatcctgg gcgaggccgt ggccccagcg    2580
catgtgccgg cacctagccc gcaaggccct ggtggcctcc aggtgcctc cacctgacac    2640
aaccgtcccc ggcccctgcc ccgcccccaa gctcggatca catgaaggag acagcagcac    2700
ccacccatgc acgcacccg cccctgcatg cctggcccct cctcctagaa aacccttccc    2760
gccctcggga agtagatgt ggagggtggc gccctgcgta accctcgccc tgtccctccc    2820
actccctggg ggcgctgttc cacagtgact gggccctgtc cagggcagtg agtcctctac    2880
tttgctccgt ggaggaagct ggggtacaag gggcccagtg ctggccacac agcagcgcag    2940
ccgagcccca ggagcccgtc aggccacagc ccctggcact gcaggtggcc tccctccaga    3000
```

-continued

```
gactcgagtc cccatgattc cctcctcgtc agtctctcaa agaccccatg gtccatcccc    3060
tgagggtggt cagccaaggc tcccgttccg tgggatgcca taaaagccgc ccagtgggac    3120
ccacagtcac acagagcgcc tcacctgcat cctctccccc acaagagccc caaagatccc    3180
acgggagagg ggagagggac gcacagcact gcctgccaag cgagaatgca ggccccgccc    3240
cctcggcccc tcaccacctc tttctacagc ctaatttatt ggattcccta ttcgtagcca    3300
tctccgtggc caatgtgact accgtgccag cagcgggggc ggcccagcct ctgagtcccg    3360
tggggccccg gctcccaccg gtgccaaacc cagcccctgc ggccgtcacc ccgccagcct    3420
acactgccag ccgccaccgg ggcacacggg cctctgcttg ccagccagga gtgcggacac    3480
catgttccca gctcagtgcc aaagaggggt caccagggggg agctgtctgc ggagccagcg    3540
cctgcccgag agagacccca ccgccaccgt gtgccttttcc cgggccctca gccctcgggc    3600
cgggcaccac ccccagtccc cccagtaaaa gcctccactg gcaaatgcag tccttcctcc    3660
ctgcaaaaaa aaaaaaaaaa aaaaaaaaaa aaaaaaa                             3697
```

<210> SEQ ID NO 10
<211> LENGTH: 745
<212> TYPE: PRT
<213> ORGANISM: Homo sapiens
<220> FEATURE:
<221> NAME/KEY: MISC_FEATURE
<223> OTHER INFORMATION: Genbank Accession No NP_000024.2

<400> SEQUENCE: 10

```
Met Pro Val Leu Ser Arg Pro Arg Pro Trp Arg Gly Asn Thr Leu Lys
1               5                   10                  15

Arg Thr Ala Val Leu Leu Ala Leu Ala Ala Tyr Gly Ala His Lys Val
            20                  25                  30

Tyr Pro Leu Val Arg Gln Cys Leu Ala Pro Ala Arg Gly Leu Gln Ala
        35                  40                  45

Pro Ala Gly Glu Pro Thr Gln Glu Ala Ser Gly Val Ala Ala Ala Lys
    50                  55                  60

Ala Gly Met Asn Arg Val Phe Leu Gln Arg Leu Leu Trp Leu Leu Arg
65                  70                  75                  80

Leu Leu Phe Pro Arg Val Leu Cys Arg Glu Thr Gly Leu Leu Ala Leu
                85                  90                  95

His Ser Ala Ala Leu Val Ser Arg Thr Phe Leu Ser Val Tyr Val Ala
            100                 105                 110

Arg Leu Asp Gly Arg Leu Ala Arg Cys Ile Val Arg Lys Asp Pro Arg
        115                 120                 125

Ala Phe Gly Trp Gln Leu Leu Gln Trp Leu Leu Ile Ala Leu Pro Ala
    130                 135                 140

Thr Phe Val Asn Ser Ala Ile Arg Tyr Leu Glu Gly Gln Leu Ala Leu
145                 150                 155                 160

Ser Phe Arg Ser Arg Leu Val Ala His Ala Tyr Arg Leu Tyr Phe Ser
                165                 170                 175

Gln Gln Thr Tyr Tyr Arg Val Ser Asn Met Asp Gly Arg Leu Arg Asn
            180                 185                 190

Pro Asp Gln Ser Leu Thr Glu Asp Val Val Ala Phe Ala Ala Ser Val
        195                 200                 205

Ala His Leu Tyr Ser Asn Leu Thr Lys Pro Leu Leu Asp Val Ala Val
    210                 215                 220

Thr Ser Tyr Thr Leu Leu Arg Ala Ala Arg Ser Arg Gly Ala Gly Thr
225                 230                 235                 240
```

```
Ala Trp Pro Ser Ala Ile Ala Gly Leu Val Val Phe Leu Thr Ala Asn
            245                 250                 255

Val Leu Arg Ala Phe Ser Pro Lys Phe Gly Glu Leu Val Ala Glu Glu
                260                 265                 270

Ala Arg Arg Lys Gly Glu Leu Arg Tyr Met His Ser Arg Val Val Ala
            275                 280                 285

Asn Ser Glu Glu Ile Ala Phe Tyr Gly Gly His Glu Val Glu Leu Ala
        290                 295                 300

Leu Leu Gln Arg Ser Tyr Gln Asp Leu Ala Ser Gln Ile Asn Leu Ile
305                 310                 315                 320

Leu Leu Glu Arg Leu Trp Tyr Val Met Leu Glu Gln Phe Leu Met Lys
                325                 330                 335

Tyr Val Trp Ser Ala Ser Gly Leu Leu Met Val Ala Val Pro Ile Ile
                340                 345                 350

Thr Ala Thr Gly Tyr Ser Glu Ser Asp Ala Glu Ala Val Lys Lys Ala
            355                 360                 365

Ala Leu Glu Lys Lys Glu Glu Glu Leu Val Ser Glu Arg Thr Glu Ala
        370                 375                 380

Phe Thr Ile Ala Arg Asn Leu Leu Thr Ala Ala Asp Ala Ile Glu
385                 390                 395                 400

Arg Ile Met Ser Ser Tyr Lys Glu Val Thr Glu Leu Ala Gly Tyr Thr
                405                 410                 415

Ala Arg Val His Glu Met Phe Gln Val Phe Glu Asp Val Gln Arg Cys
            420                 425                 430

His Phe Lys Arg Pro Arg Glu Leu Glu Asp Ala Gln Ala Gly Ser Gly
        435                 440                 445

Thr Ile Gly Arg Ser Gly Val Arg Val Glu Gly Pro Leu Lys Ile Arg
        450                 455                 460

Gly Gln Val Val Asp Val Glu Gln Gly Ile Ile Cys Glu Asn Ile Pro
465                 470                 475                 480

Ile Val Thr Pro Ser Gly Glu Val Val Ala Ser Leu Asn Ile Arg
                485                 490                 495

Val Glu Glu Gly Met His Leu Leu Ile Thr Gly Pro Asn Gly Cys Gly
                500                 505                 510

Lys Ser Ser Leu Phe Arg Ile Leu Gly Gly Leu Trp Pro Thr Tyr Gly
        515                 520                 525

Gly Val Leu Tyr Lys Pro Pro Pro Gln Arg Met Phe Tyr Ile Pro Gln
        530                 535                 540

Arg Pro Tyr Met Ser Val Gly Ser Leu Arg Asp Gln Val Ile Tyr Pro
545                 550                 555                 560

Asp Ser Val Glu Asp Met Gln Arg Lys Gly Tyr Ser Glu Gln Asp Leu
                565                 570                 575

Glu Ala Ile Leu Asp Val Val His Leu His His Ile Leu Gln Arg Glu
            580                 585                 590

Gly Gly Trp Glu Ala Met Cys Asp Trp Lys Asp Val Leu Ser Gly Gly
            595                 600                 605

Glu Lys Gln Arg Ile Gly Met Ala Arg Met Phe Tyr His Arg Pro Lys
        610                 615                 620

Tyr Ala Leu Leu Asp Glu Cys Thr Ser Ala Val Ser Ile Asp Val Glu
625                 630                 635                 640

Gly Lys Ile Phe Gln Ala Ala Lys Asp Ala Gly Ile Ala Leu Leu Ser
                645                 650                 655
```

```
Ile Thr His Arg Pro Ser Leu Trp Lys Tyr His Thr His Leu Leu Gln
            660             665             670

Phe Asp Gly Glu Gly Gly Trp Lys Phe Glu Lys Leu Asp Ser Ala Ala
        675             680             685

Arg Leu Ser Leu Thr Glu Glu Lys Gln Arg Leu Glu Gln Gln Leu Ala
        690             695             700

Gly Ile Pro Lys Met Gln Arg Arg Leu Gln Glu Leu Cys Gln Ile Leu
705             710             715             720

Gly Glu Ala Val Ala Pro Ala His Val Pro Ala Pro Ser Pro Gln Gly
            725             730             735

Pro Gly Gly Leu Gln Gly Ala Ser Thr
        740             745
```